(12) United States Patent
Liu et al.

(10) Patent No.: US 12,079,208 B2
(45) Date of Patent: Sep. 3, 2024

(54) DATA PROCESSING METHOD, APPARATUS, AND DEVICE

(71) Applicant: Alibaba Group Holding Limited, Grand Cayman (KY)

(72) Inventors: Wei Liu, Hangzhou (CN); Yu Wang, Hangzhou (CN); Chao Liu, Hangzhou (CN); Ying Chi, Hangzhou (CN); Xuansong Xie, Hangzhou (CN); Xiansheng Hua, Hangzhou (CN)

(73) Assignee: ALIBABA GROUP HOLDING LIMITED, Grand Cayman (KY)

( * ) Notice: Subject to any disclaimer, the term of this patent is extended or adjusted under 35 U.S.C. 154(b) by 960 days.

(21) Appl. No.: 16/929,365

(22) Filed: Jul. 15, 2020

(65) Prior Publication Data
US 2021/0057058 A1 Feb. 25, 2021

(30) Foreign Application Priority Data
Aug. 23, 2019 (CN) .......................... 201910784288.9

(51) Int. Cl.
*G06F 16/242* (2019.01)
*G06F 16/2457* (2019.01)
*G06F 16/248* (2019.01)
*G06F 16/901* (2019.01)

(52) U.S. Cl.
CPC ...... *G06F 16/243* (2019.01); *G06F 16/24573* (2019.01); *G06F 16/248* (2019.01); *G06F 16/9024* (2019.01)

(58) Field of Classification Search
CPC ............. G06F 16/243; G06F 16/24573; G06F 16/248; G06F 16/9024
See application file for complete search history.

(56) References Cited

U.S. PATENT DOCUMENTS

| | | | |
|---|---|---|---|
| 4,893,271 A | 1/1990 | Davis et al. | |
| 7,818,177 B1 | 10/2010 | Bangalore et al. | |
| 8,381,124 B2 | 2/2013 | Martin et al. | |
| 8,843,852 B2 | 9/2014 | Berry et al. | |
| 9,239,872 B2* | 1/2016 | Casella dos Santos | ..................... G06F 16/285 |
| 9,633,282 B2* | 4/2017 | Sharma | .................. G06V 10/56 |
| 9,786,051 B2* | 10/2017 | Harper | .................. G16H 30/40 |
| 10,096,382 B2 | 10/2018 | Zhu et al. | |
| 10,740,866 B2* | 8/2020 | Katouzian | .............. G06N 3/045 |

(Continued)

FOREIGN PATENT DOCUMENTS

JP 5674457 B2 2/2015

*Primary Examiner* — Miranda Le
(74) *Attorney, Agent, or Firm* — James J. DeCarlo; Greenberg Traurig, LLP

(57) ABSTRACT

Embodiments of the disclosure provide a method, apparatus, and device for data processing. The method comprises: obtaining data of at least two different modalities, the data comprising at least first data and second data, the first data and second stored in respective data sources; determining an overlapping keyword correlating the first data and the second data by analyzing textual descriptions associated with the first data and second data and identifying the overlapping keyword as appearing in a textual description of the first data and in a textual description of the second data; and storing the first data and the second data in an associative manner based on the overlapping keyword, the associative manner generated using the overlapping keyword.

17 Claims, 18 Drawing Sheets

(56) References Cited

U.S. PATENT DOCUMENTS

| | | | |
|---|---|---|---|
| 11,037,309 B2* | 6/2021 | Cheng | G06N 20/00 |
| 11,699,236 B2* | 7/2023 | Avital | G01R 33/5608 |
| | | | 382/131 |
| 2006/0004278 A1* | 1/2006 | Giger | G06T 7/35 |
| | | | 600/408 |
| 2008/0243539 A1 | 10/2008 | Barish et al. | |
| 2008/0275913 A1* | 11/2008 | van Arragon | G16H 15/00 |
| 2009/0082637 A1* | 3/2009 | Galperin | G16H 30/20 |
| | | | 600/300 |
| 2009/0092298 A1 | 4/2009 | Xu et al. | |
| 2009/0132254 A1 | 5/2009 | Fitzgerald et al. | |
| 2010/0228692 A1* | 9/2010 | Guralnik | G06V 10/768 |
| | | | 706/54 |
| 2011/0119089 A1 | 5/2011 | Carlisle | |
| 2011/0161854 A1 | 6/2011 | Shukla | |
| 2013/0046529 A1 | 2/2013 | Grain et al. | |
| 2013/0110547 A1 | 5/2013 | Englund et al. | |
| 2014/0149407 A1* | 5/2014 | Qian | G06F 16/35 |
| | | | 707/758 |
| 2014/0188514 A1* | 7/2014 | Balignasay | G16H 10/60 |
| | | | 705/3 |
| 2016/0071264 A1* | 3/2016 | Agam | G06V 10/774 |
| | | | 382/128 |
| 2017/0300634 A1 | 10/2017 | Chiang et al. | |
| 2018/0089392 A1 | 3/2018 | Janevski et al. | |
| 2019/0209116 A1* | 7/2019 | Sjöstrand | G16H 50/30 |
| 2021/0038188 A1* | 2/2021 | Lahti | A61B 5/742 |

* cited by examiner

DATA PROCESSING METHOD, APPARATUS, AND DEVICE

CROSS-REFERENCE TO RELATED APPLICATIONS

The present application claims priority to Chinese Patent Application No. 201910784288.9, filed on Aug. 23, 2019, which is incorporated herein by reference in its entirety

BACKGROUND

Technical Field

The disclosure relates to the field of data processing technologies, and in particular, to a data processing method, apparatus, and device.

Description of Related Art

With the rapid development of science and technology, digitization of information has become prevalent in various areas of human lives. Digitization of information has wide applications, especially in the fields of e-commerce, education, healthcare, etc.

Using the field of medical healthcare as an example, presently, most medical data is stored in a hospital information system (HIS). In general, a HIS includes a picture archiving and communication system (PACS), a radiology information system (RIS), a clinical information system (CIS), a laboratory information system (LIS), an electronic medical record (EMR) system, and the like. These systems are mainly configured for digital storage and management of medical data.

However, the above-described various data systems are not entirely in open communication with each other. As a result, data of different modalities stored in different medical information systems lack correlation with each other, and data chains of patients break during treatment. Moreover, there are isolated information islands among hospitals causing medical data to be scattered across the hospitals. As a result, organizations are not being able to perform unified data management or execute applications on data of different modalities.

SUMMARY

Embodiments of the disclosure provide data processing methods, apparatuses, and devices to perform structured storage on data of different modalities so as to achieve unified storage and management of data of different modalities.

In one embodiment, the disclosure provides a data processing method, the method comprising obtaining data of at least two different modalities for processing, the data comprising at least first data and second data; determining one or more keywords correlating the first data and the second data; and storing the first data and the second data in an associative manner based on the one or more keywords.

In one embodiment, the disclosure provides a data processing apparatus, the apparatus comprising: a first obtaining module configured to obtain data of at least two different modalities for processing, the data comprising at least first data and second data; a first determining module configured to determine one or more keywords correlating the first data and the second data; and a first processing module configured to store the first data and the second data in an associative manner based on the one or more keywords.

In one embodiment, the disclosure provides an electronic device, the electronic device comprising: a memory and a processor, wherein the memory is configured to store one or more computer instructions, when executed by the processor, instructing the electronic device to perform the data processing method as described above.

In one embodiment, the disclosure provides a computer storage medium for storing a computer program, wherein the computer program causes a computer to implement the data processing method as described above.

According to various embodiments, first data and second data of at least two different modalities is obtained, one or more keywords correlating the first data and the second data is determined such that the first data and the second data is stored in an associative manner based on the one or more keywords. This way, the structured storage of data of different modalities is effectively performed to achieve unified storage and management of data of different modalities. As a result, it becomes more convenient for a user to retrieve and apply stored data subsequent to data storage, thereby further improving the practical application of the disclosed methods, and contributing to market promotion and adoption.

In one embodiment, the disclosure provides a data processing method, the method comprising: obtaining a data search request, the data search request being used for performing data searches on data of at least two different modalities; determining at least one data search model corresponding to the data search request; and determining at least one search result corresponding to the data search request using the data search model.

In one embodiment, the disclosure provides a data processing apparatus, the apparatus comprising: a second obtaining module configured to obtain a data search request, the data search request being used for performing data searches on data of at least two different modalities; a second determining module configured to determine at least one data search model corresponding to the data search request; and a second processing module configured to determine at least one search result corresponding to the data search request using the data search model.

In one embodiment, the disclosure provides an electronic device, the electronic device comprising: a memory and a processor, wherein the memory is configured to store one or more computer instructions, when executed by the processor, instructing the electronic device to perform the data processing method as described above.

In one embodiment, the disclosure provides a computer storage medium for storing a computer program, wherein the computer program causes a computer to perform the data processing method as described above.

With the methods provided by embodiments of the disclosure, a data retrieval request is obtained; at least one data search model corresponding to the data search request is determined; and at least one retrieval result corresponding to the data search request is determined using the data search model. This way, different data search models are effectively determined based on different data search requests such that to improve the quality and efficiency of data searches using different data search models, further improving the practical applications of the methods and facilitating market promotion and adoption.

BRIEF DESCRIPTION OF THE DRAWINGS

To describe the technical solutions in the embodiments of the disclosure clearly, drawings to be used for the description of the embodiments are briefly introduced below. The drawings in the following description are some embodiments of the disclosure. Those of ordinary skill in the art can further obtain other accompanying drawings according to these accompanying drawings without significant efforts.

DETAILED DESCRIPTION

Figure 1A:
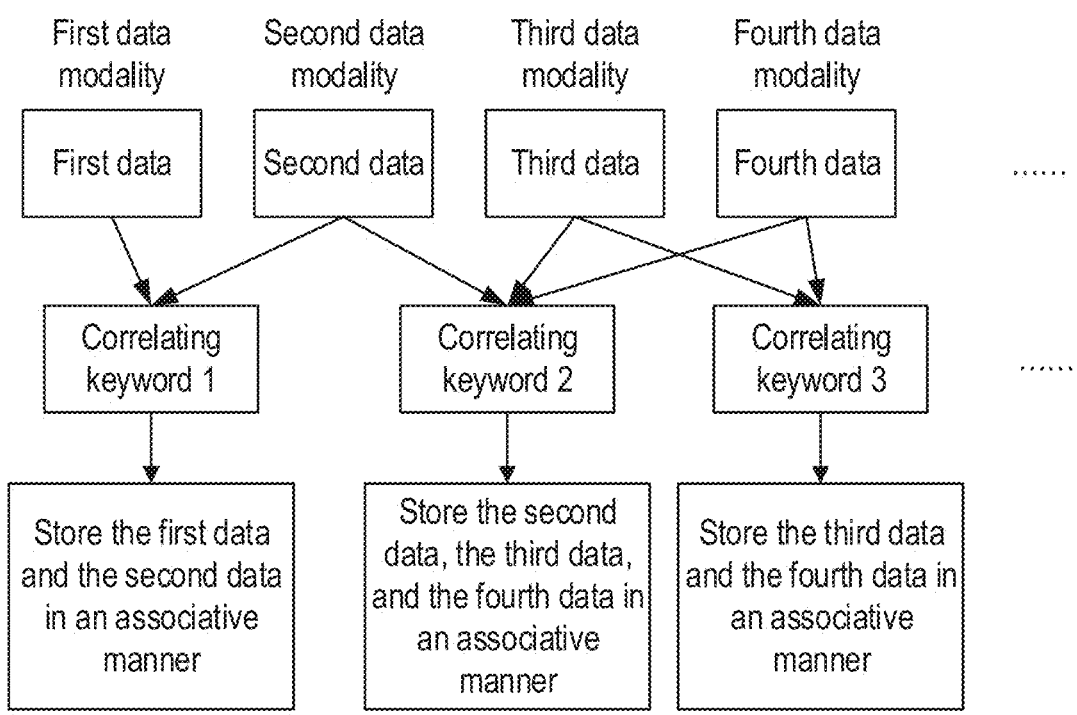
FIG. 1A is a schematic diagram illustrating a data processing method according to some embodiments of the disclosure.

To make the purposes, technical solutions, and advantages of the embodiments of the disclosure clearer, the technical solutions in the embodiments of the disclosure will be described clearly and completely below with reference to the drawings in the embodiments of the disclosure. The embodiments described herein are merely some, rather than all of the embodiments, of the disclosure. Based on the embodiments in the disclosure, all other embodiments obtained by those of ordinary skill in the art without making significant efforts shall fall within the scope of the disclosure.

The terminology used in the embodiments of the disclosure is for the purpose of describing particular embodiments only and is not intended to limit the disclosure. The singular forms "a," "said," and "the" used in the embodiments of the disclosure and the appended claims are also intended to include the plural forms unless the context clearly indicates another meaning. For "a plurality of," at least two are included generally, but the case where at least one is included is not excluded.

It should be understood that the term "and/or" used herein is merely used for describing an association relationship of associated objects, and indicates that three relationships can exist. For example, A and/or B can indicate the following three cases: A exists alone, both A and B exist, and B exists alone. In addition, the character "/" herein generally indicates that the associated objects before and after it are in an "or" relationship.

Depending on the context, the words "if" and "in case of" as used herein can be interpreted as "at the time . . . " or "when . . . " or "in response to the determination" or "in response to the detection." Similarly, depending on the context, the phrase "if it is determined" or "if (the stated condition or event) is detected" can be interpreted as "when it is determined" or "in response to the determination" or "when (the stated condition or event) is detected" or "in response to the detection of (the stated condition or event)."

It should also be noted that the terms "include," "comprise," or any other variation thereof are intended to encompass non-exclusive inclusions, so that a commodity or system including a series of elements includes not only those elements but also other elements that are not explicitly listed, or includes elements that are inherent to this commodity or system. Without more restrictions, an element defined by the sentence "including a(n) . . . " does not exclude the existence of another identical element in the commodity or system that includes the element.

In addition, some processes described herein or depicted in the drawings include a plurality of operations occurring in a specific sequence. However, these operations may not be performed in the specific sequence depicted or may be performed in parallel. An operational sequence only serves as an illustrating example, not intended as a limitation in any manner.

As used herein, multi-modal data refers to a collective label for data that is of at least two different modalities and relates to a specific field. Using the field of healthcare as an example, multi-modal medical data includes, for example, daily data of patients generated at institutions such as hospitals, physical examination centers, and specialist clinics. Such data includes various image data (e.g., X-Ray, CT, MRI, and pathological sections slide information), various written records (e.g., image reports, examination indices, treatment plans, and follow-up records), as well as intermediary data generated by auxiliary diagnostic and treatment tools, and the like. Such multi-modal data further includes, for example, medical knowledge data published by doctors, researchers in colleges and universities, and the like. For instance, medical knowledge data includes papers, Patents, and survey reports.

To facilitate understanding of the technical solutions provided by the disclosure, the current technology is illustrated below briefly.

Digitization of information has progressed with full advancement into various areas of human lives. Digitization of information has wider applications, especially in the fields of e-commerce, education, healthcare, and so on. Using the field of healthcare as an example, presently, most medical data is stored in a hospital information system (HIS). In general, a HIS includes a picture archiving and communication system (PACS), a radiology information system (RIS), a clinical information system (CIS), a laboratory information system (LIS), an electronic medical record (EMR), and the like. These systems are mainly configured for digital storage and management of medical data.

Further, current HIS systems are mainly used for digital storage of data, thus providing only simplified data management functions. For example, a user can only query a database by keywords or label selection, leading to oftentimes unsatisfactory search results, and requiring further manual screening to find the searched-for target. If a portion of some labels associated with some image data is missing, the image data is never to be retrieved. Furthermore, such an HIS system rarely provides any function to further analyze search results as a result of which the user has to export data for cleaning and/or modeling analysis, wasting time and effort.

The above-described dilemma is mainly caused by the following two reasons. First, such data of different modalities is separately stored in inconsistent storage forms, some of which are structured (e.g., Digital Imaging and Communications in Medicine (DICOM) images), and some of which are unstructured (e.g., medical record reports). There are no unified formats to structure data and connect the entire medical data chains. Thus, fusion processing cannot be performed on the multi-modal data. Second, the current management of medical data is separate from the analysis of medical data. The management provides only basic search functions such as data addition, deletion, search, and modification. While for analysis, result data is exported out of the system for remodeling, leading to insufficient medical data utilization.

Figure 1B:
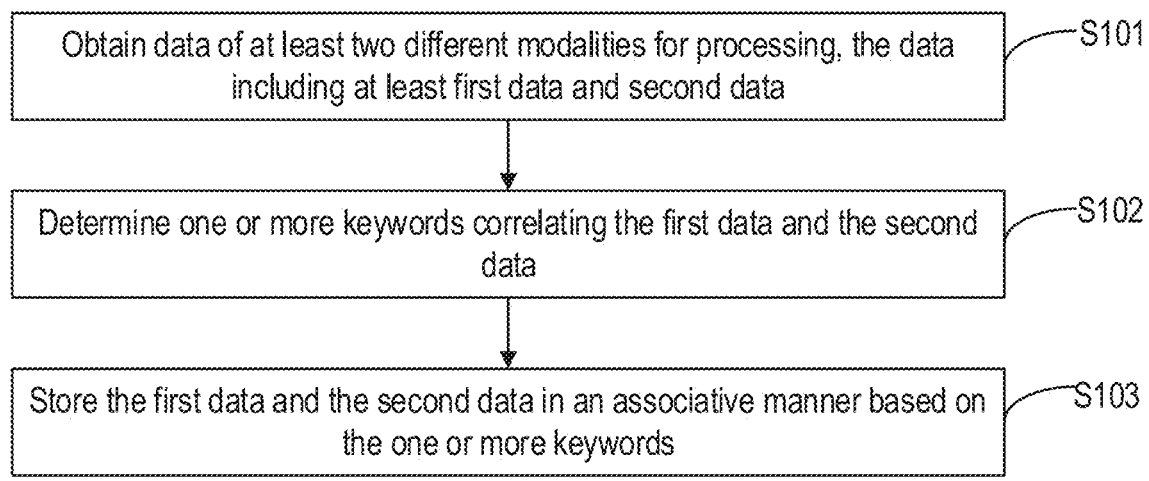
FIG. 1B is a flow diagram illustrating a data processing method according to some embodiments of the disclosure.

FIG. 1A is a schematic diagram illustrating a data processing method according to some embodiments of the disclosure. FIG. 1B is a flow diagram illustrating a data processing method according to some embodiments of the disclosure. The following illustrates a data processing method with reference to FIGS. 1A through 1B. In some embodiments, the data processing method is performed by a data processing apparatus, which can be implemented as a software, hardware, or a combination thereof. In one embodiment, as shown in FIG. 1A, the data processing method includes the following steps.

Step S101: obtain data of at least two different modalities for processing, the data including at least first data and second data.

As used herein, the data of at least two different modalities refers to data of at least two different data types or at least two different data states. To illustrate, in one example, such data includes at least first data and second data. In this case, the first data and the second data is of different data modalities. For instance, in the field of healthcare, the first data includes a physical examination report; and the second data includes a CT image, where a physical examination report and a CT image are data obtained as different data modalities. For another example, such first data is a CT image, and such second data is an MRI image. In this case, the first data and the second data is also data of two different modalities for processing.

In some embodiments, the data for processing includes a plurality of items of data which comprises data of at least two different modalities. For example, the data includes first data, second data, and third data. Here, the first data and the second data corresponds to a first data modality, and the third data corresponds to a second data modality. In another example as shown in FIG. 1A, the data includes first data, second data, third data, or fourth data. In this case, a data modality corresponding to the first data is a first data modality; a data modality corresponding to the second data is a second data modality; a data modality corresponding to the third data is a third data modality; and a data modality corresponding to the fourth data is a fourth data modality. Those skilled in the art can configure the data for processing in any suitable manner based on specific application requirements.

Further, manners to obtain the data of at least two different modalities are not limited by the embodiments or in any other way. For example, those skilled in the art can configure the manners based on specific application scenarios and requirements. In one example, the first data and second data of different data modalities is obtained using data acquisition apparatuses, which is communicatively coupled to a processing apparatus such that the processing apparatus obtains the first data and second data of different data modalities. In some embodiments, the first data and second data is directly transmitted to the processing apparatus by a user such that the processing apparatus stably and effectively obtains the first data and the second data.

Step S102: determine one or more keywords correlating the first data and the second data.

In this example, after the first data and the second data is obtained, first description information corresponding to the first data and second description information corresponding to the second data is obtained. Based on the first description information and the second description information, one or more keywords correlating the first data and the second data is determined. In some embodiments, the one or more keywords are the same keyword information that is included among both the first description information and the second description information. According to various embodiments, the one or more correlating keywords are adjusted and changed based on different application scenarios and requirements.

The following illustrates the above-described keywords with an example in the field of healthcare. In this example, the first data is test data of a user A at a hospital, and the second data is physical examination data of user A at a physical examination center. After the first data and the second data is obtained, it is determined that the keyword correlating the first data and the second data is "user A" based on the analyzing and identifying of the first data and the second data. In this case, the correlating keyword is the user identification information.

Further, in another example, the first data is the test data of user A at a first hospital, and the second data is the test data of a user B at the first hospital. In this case, after the first data and the second data is obtained, it is determined that the keyword correlating the first data and the second data is "first hospital" based on the analyzing and identifying of the first data and the second data. Here, the correlating keyword is the hospital identification information.

According to various embodiments, the data for processing includes data of at least two different modalities in any field such as education, finance, etc. Different fields are selected for applications based on application requirements. In one example, the first data is the education information indicating a user A receiving education in a first school, and the second data is the education information indicating user A receiving education in a second school. In this case, the keyword correlating the first data and the second data is "user A." In another example, the first data is the education information indicating user A receiving education in a first school, and the second data is the education information indicating a user B receiving education in the first school. Here, the keyword correlating the first data and the second data is "first school."

Step S103: store the first data and the second data in an associative manner based on the one or more keywords.

After the one or more keyword are obtained, the first data and the second data is stored in an associative manner based on the one or more keywords such that a correlative relationship is established between the first data and the second data to facilitate later searches for and use of the first data and the second data based on the one or more correlating keyword.

According to various embodiments, when the data includes a plurality of items of data, and a plurality of correlating keywords correspond to the plurality of items of data, the correlated data is stored in an associative manner based on the correlating keywords. As shown in FIG. 1A, the data includes first data, second data, third data, and fourth data. Here, the first data and the second data correspond to a correlating keyword 1; the second data, the third data, and the fourth data correspond to a correlating keyword 2; the third data and the fourth data correspond to a correlating keyword 3. In this example, the first data and the second data is stored in an associative manner based on the correlating keyword 1; the second data, the third data, and the fourth data is stored in an associative manner according to the correlating keyword 2; the third data and the fourth data is stored in an associative manner based on the correlating keyword 3.

With the data processing methods provided by embodiments of the disclosure, first data and second data of at least two different modalities is obtained, and one or more keywords correlating the first data and the second data is determined such that the first data and the second data is stored in an associative manner based on the one or more keywords. This way, structured storage of data of different modalities is effectively achieved; unified storage and management of data of different modalities is facilitated, making it convenient for a user to search and apply stored data. As such, practical applications of the methods are improved, leading to market promotion and adoption.

Figure 2:
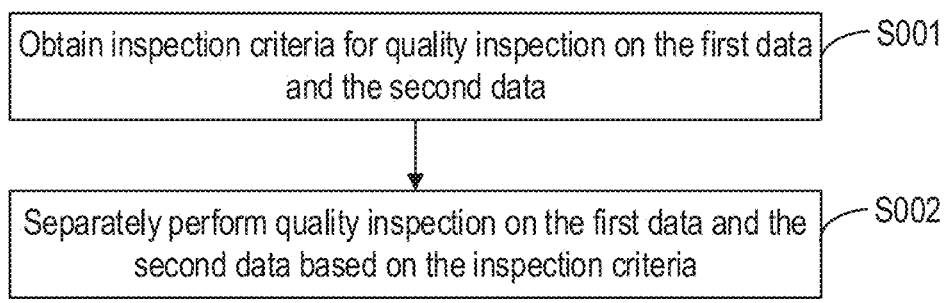
FIG. 2 is a flow diagram illustrating a data processing method according to some embodiments of the disclosure.

FIG. 2 is a flow diagram illustrating a data processing method according to some embodiments of the disclosure. As shown in FIG. 2, based on the above-described embodiments, to ensure the effectiveness of associative storage of the first data and the second data, before storing the first data and the second data in an associative manner based on the one or more keywords, the method further includes the following steps.

Step S001: obtain inspection criteria for quality inspecting on the first data and the second data.

In some embodiments, the inspection criteria are pre-configured criteria information for data quality inspection. In the scenarios of healthcare, the inspection criteria are unified evaluation criteria set based on medical guidelines and doctors' opinions. In various embodiments, different inspection criteria are set with different medical guidelines and doctors' opinions. The quality of the first data and the second data is evaluated based on the inspection criteria such that it is identified whether the first data and the second data is qualified data.

Step S002: separately perform quality inspection on the first data and the second data based on the inspection criteria.

In some embodiments, after the inspection criteria are obtained, quality inspections are separately performed on the first data and the second data using the inspection criteria. In one embodiment, separately performing quality inspection on the first data and the second data based on the inspection criteria includes the following sub-steps.

Sub-step S0020: inspect whether the first data and/or the second data meets the inspection criteria.

Sub-step S0021: determine that the first data and/or the second data is qualified data when the first data and/or the second data meets the inspection criteria.

Sub-step S0022: determine that the first data and/or the second data is unqualified data when the first data and/or second data does not meet the inspection criteria.

In some embodiments, the inspection criteria include a plurality of evaluation principles for data quality inspection. After the first data, the second data, and the inspection criteria are obtained, inspection is performed to determine whether the first data and/or the second data meets the evaluation principles included in the inspection criteria. If the first data and/or the second data meets the inspection criteria, it indicates that the first data and/or the second data is qualified data. Otherwise, the first data or the second data is unqualified data. In implementations, the first quality evaluation information corresponding to the first data with respect to the inspection criteria is obtained. When the first quality evaluation information is greater than or equal to a preset threshold, it is determined that the first data meets the inspection criteria. When the first quality evaluation information is less than the preset threshold, it is determined that the first data does not meet the inspection criteria. Similarly, the second quality evaluation information corresponding to the second data with respect to the inspection criteria is obtained. When the second quality evaluation information is greater than or equal to a preset threshold, it is determined that the second data meets the inspection criteria. When the second quality evaluation information is less than the preset threshold, it is determined that the second data does not meet the inspection criteria.

According to various embodiments, the method further includes the following sub-steps.

Sub-step S0023: upon determining that at least one of the first data and the second data is unqualified data, delete the unqualified data.

After determining that either the first data or the second data is unqualified data, or both the first data and the second data is unqualified data, to improve the quality of the data stored, such unqualified data is deleted.

Sub-step S0024: after determining that the first data and the second data is both qualified data, allow first data and the second data to be stored in an associative manner based on the correlating keyword(s).

After it is determined that the first data and the second data are both qualified data, and as qualified data of different modalities identifies each other, an associative storing operation is performed on the first data and the second data based on the correlating keyword(s). That is, data subjected to the associative storing operation is qualified data, ensuring the quality of the stored data.

Figure 3:
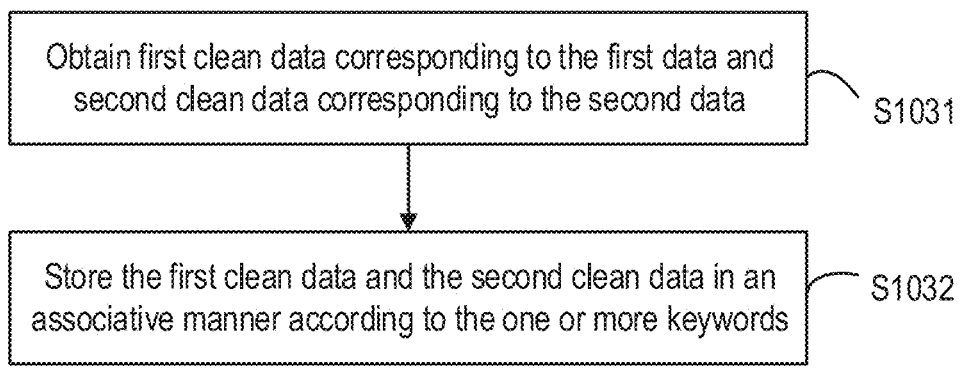
FIG. 3 is a flow diagram illustrating a method for storing first data and the data in an associative manner based on keywords, according to some embodiments of the disclosure.
Figure 4:
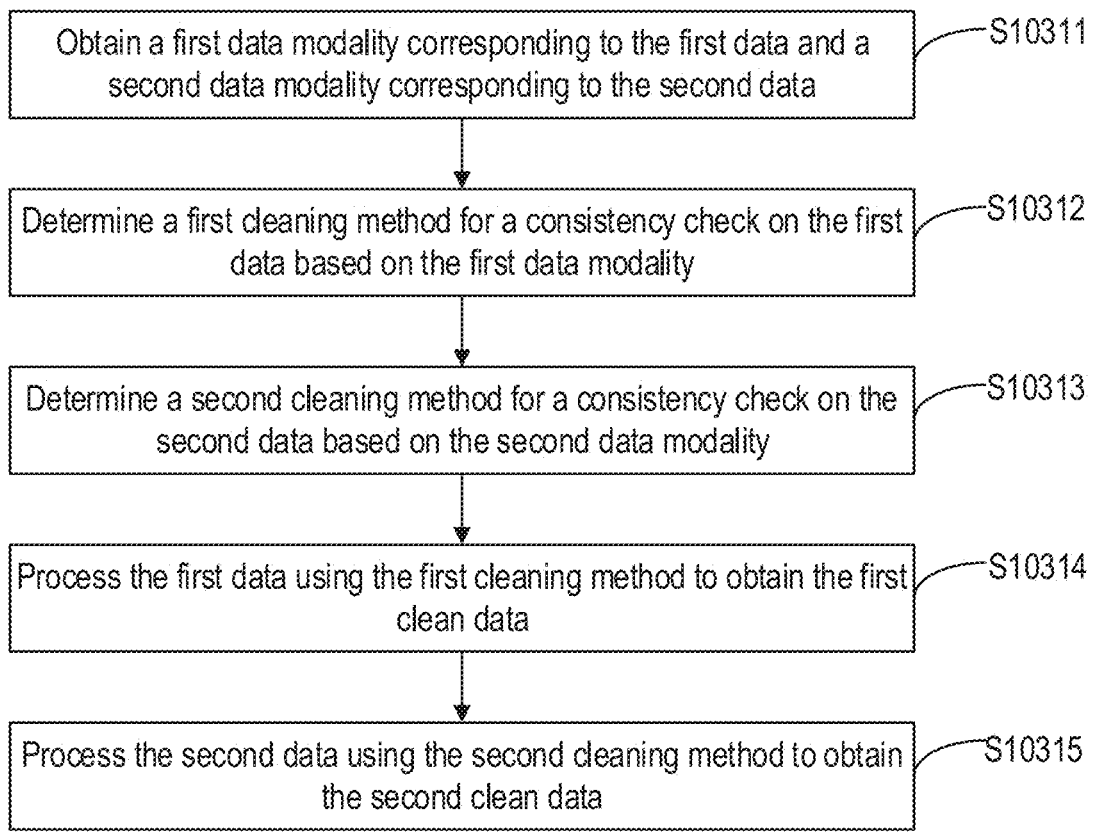
FIG. 4 is a flow diagram illustrating a method for obtaining first clean data corresponding to the first data and second clean data corresponding to the second data according to some embodiments of the disclosure.

FIG. 3 is a flow diagram illustrating a method for storing the first data and the second data in an associative manner based on the correlating keyword(s) according to some embodiments of the disclosure. FIG. 4 is a flow diagram illustrating a method for obtaining first clean data corresponding to the first data and second clean data corresponding to the second data according to some embodiments of the disclosure. Any suitable techniques can be utilized to, without limitations, store the first data and second data based on the correlating keyword(s) in association with each other. For example, it can be based on application requirements and design requirements. In some embodiments, as shown in FIGS. 3 and 4, and based on the above-described embodiments, a method for storing the first data and the second data in an associative manner based on the correlating keyword(s) includes the following steps.

Step S1031: obtain first clean data corresponding to the first data and second clean data corresponding to the second data.

The first clean data is the data obtained after a cleaning operation is performed on the first data; and the second clean data is the data obtained after a cleaning operation is performed on the second data. In one embodiment, the obtaining of the first clean data corresponding to the first data and the second clean data corresponding to the second data includes and the following sub-steps.

Sub-step S10311: obtain a first data modality corresponding to the first data and a second data modality corresponding to the second data.

As the first data and the second data is of different data modalities, data of different data modalities corresponds to different data cleaning methods for consistency checks on data. Thus, to clean the first data and the second data, a first data modality corresponding to the first data and a second data modality corresponding to the second data are obtained first. Any suitable techniques can be used to obtain the first data modality and the second data modality, without limitation, based on application scenarios and service scenarios. In one example, the first data modality and the second data modality are identified through a pre-configured modal analysis algorithm. In another example, the data modality information corresponding to the first data is obtained. Then, the data modality information is analyzed and compared with a plurality of pre-stored standard modality information. As a result, a data modality corresponding to the standard modality information that matches the data modality information is determined as the first data modality. The second data modality is obtained in a similar manner.

According to various embodiments, the first data modality and the second data modality can be obtained in any suitable manner, as long as the accuracy and reliability of the first data modality and the second data modality is guaranteed.

Sub-step S10312: determine a first cleaning method for a consistency check on the first data based on the first data modality.

In one embodiments, after the first data modality is obtained, a first cleaning method is determined using a pre-stored mapping relationship between the data modalities and cleaning methods. The first cleaning method is used for a consistency check on the first data. In one example, the consistency check includes at least one of the following operations: a de-duplication operation, an error correction operation, a conversion operation, an operation of checking and adding of missing data, and the like. This way, the first data is checked for consistency, after which the first clean data capturing a set of information that is relatively complete is obtained.

Sub-step S10313: determine a second cleaning method for a consistency check on the second data based on the second data modality.

In one embodiment, after the second data modality is obtained, a second cleaning method is determined using the pre-stored mapping relationship between the data modalities and cleaning methods. The second cleaning method is used for a consistency check on the second data. In one example, the consistency check includes at least one of the following operations: a de-duplication operation, an error correction operation, a conversion operation, an operation of checking and adding of missing data, and on the like. This way, the second data is checked for consistency, after which the second clean data capturing a set of information that is relatively complete is obtained.

Sub-step S10314: process the first data using the first cleaning method to obtain the first clean data.

Sub-step S10315: process the second data using the second cleaning method to obtain the second clean data.

Sub-step S1032: store the first clean data and the second clean data in an associative manner based on the correlating keyword(s).

After the first clean data and the second clean data is obtained, the first clean data and the second clean data is stored in an associative manner based on the correlating keyword(s). Thus, a correlating relationship is established between the first clean data and the second clean data to achieve the associative storage of data that is of different modalities and yet relatively complete with expressions, facilitating later searches for and use of the first clean data and the second clean data based on the correlating keyword(s).

Figure 5:
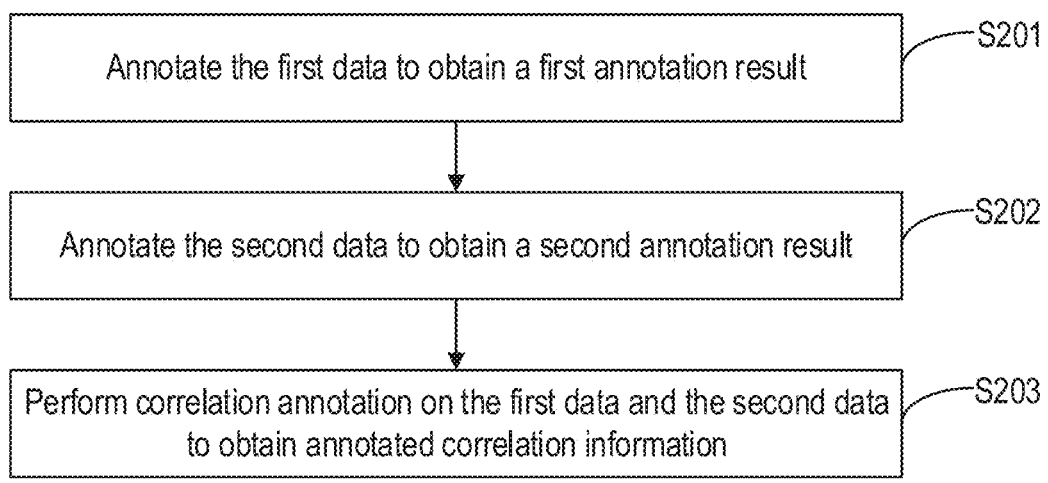
FIG. 5 is a flow diagram illustrating a data processing method according to some embodiments of the disclosure.

FIG. 5 is a flow diagram illustrating a data processing method according to some embodiments of the disclosure. As shown in FIG. 5, and based on the above-described, after storing the first data and the second data in an associative manner based on the correlating keyword(s), the method further includes the following steps.

Step S201: annotate the first data to obtain a first annotation result.

In some embodiments, after the first data and the second data is stored in an associative manner, the first data is annotated. The first data is annotated to obtain different first annotation results are based on various application scenarios/contexts. For example, when the first data is image data, the foci information in the image is annotated to obtain a first annotation result corresponding to the image data. For another example, when the first data is an image report, the disease types indicated in the image report is annotated to obtain a first annotation result corresponding to the image report. For yet another example, when the first data is examination indices, one or more extraction operations are performed with regard to one or more parameters in the examination indices to obtain a first annotation result corresponding to the examination indices. In some embodiments, the first annotation result is obtained by extracting key information of the first data.

Step S202: annotate the second data to obtain a second annotation result.

In implementations, the annotating of the second data is substantially similar to the afore-described processes for annotating the first data, the details of which are not repeated for the purpose of simplicity.

In some embodiments, the execution order illustrated in the above-described sequence varies. For example, in some scenarios, step S202 is performed before step S201, or step S202 is performed in parallel with step S201.

Step S203: perform correlation annotation on the first data and the second data to obtain annotated correlation information.

After the first data and the second data is stored in an associative manner based on the correlating keyword(s), the correlation between the first data and the second data is annotated to obtain annotated correlation information. For example, when the first data is CT image data of the lungs of a user, and the second data is MRI image data of the lungs of the same user, the foci information in the CT image data, and/or the foci information in the MRI image data, and/or the correlation between the foci in the CT image data and the foci in the MRI image data is annotated to obtain annotated correlation information about the foci information among the CT image data and the MRI image data. As such, the accuracy and reliability in determining foci information is improved.

According to various embodiments, the execution order illustrated in the afore-described sequence varies. For example, in some scenarios, step S203 is performed before steps S201 and S202, or step S203 is performed in parallel with steps S201 and S202.

Via annotating the first data, the second data, and the correlation between the first data and the second data, a first annotation result of the first data, a second annotation result of the second data, and annotated correlation information is obtained. As a result, it is convenient for the user to search and view the first data and/or the second data via the annotation results, thereby ensuring the accuracy and reliability of data retrieval.

Figure 6:
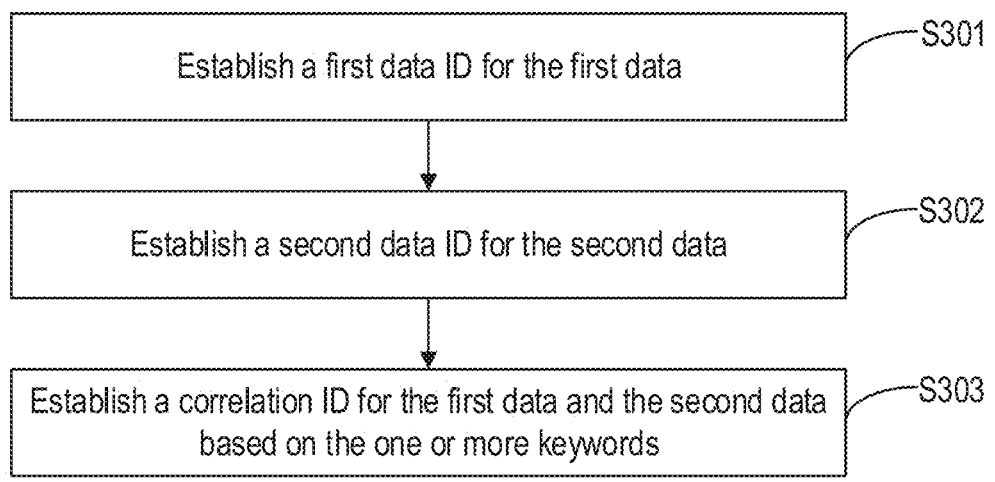
FIG. 6 is a flow diagram illustrating a data processing method according to some embodiments of the disclosure.

FIG. 6 is a flow diagram illustrating a data processing method according to some embodiments of the disclosure. As shown in FIG. 6, and based on the above-described embodiments, the method further includes the following steps.

Step S301: establish a first data ID for the first data.

Step S302: establish a second data ID for the second data.

Step S303: establish a correlation ID for the first data and the second data based on the correlating keyword(s).

In some embodiments, to facilitate searches and applications of the first data and the second data, corresponding data IDs are established for the first data and the second data, respectively, A correlation ID is also established for the first data and the second data based on the correlating keyword (s). As such, the data IDs and the correlation ID facilitate accurate and effective searches for and use of data by users. In one example, the first data is CT image data of a user A, and the second data is an image report (or data of another modality related to the CT image data) of user A. In this case, an image data ID is established for the CT image data, a report data ID is established for the image report, and a correlation ID is established based on the correlating keyword "user A," which exists among the first data and the second data, namely, image data-user A ID and report data-user A ID.

Via respective data IDs established for the first data and the second data, and a correlation ID established for the first data and the second data, CT image data corresponding to the first data is quickly retrieved, and an image report or data of another modality associated with the CT image data is also quickly found based on the correlating keyword(s) during image data searches. That is, associative data of different modalities is searched via the data IDs and the correlation keyword(s), further improving the quality and efficiency of data searches.

Figure 7:
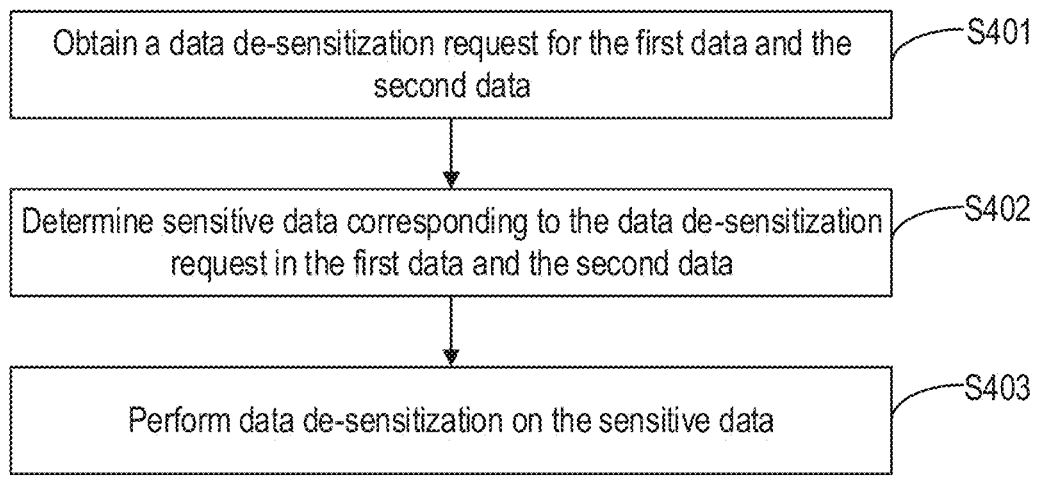
FIG. 7 is a flow diagram illustrating a data processing method according to some embodiments of the disclosure.

FIG. 7 is a flow diagram illustrating a data processing method according to some embodiments of the disclosure. As shown in FIG. 7, and based on the above-described embodiments, to ensure the security and reliability of data use, the method further includes the following steps.

Step S401: obtain a data de-sensitization request for the first data and the second data.

Step S402: determine sensitive data corresponding to the data de-sensitization request in the first data and the second data.

Step S403: perform data de-sensitization on sensitive data.

After the first data and the second data is obtained, as the first data and the second data includes some information involving personal privacy, data de-sensitization is performed on sensitive data based on a data desensitization request made by a user. For example, from a patient's perspective, the patient information, doctor information, and hospital information all entail personal private information. In some embodiments, first, the sensitive data included in the first data and the second data is based on a data de-sensitization request. After the sensitive data is obtained, a data de-sensitization operation is performed on the sensitive data based on a preset algorithm, thereby ensuring the security and reliability of the use of the sensitive data.

In one example, the first data and the second data is medical data gathered from different places or regions to facilitate multi-site consultation and selective data sharing. Further, in terms of sharing data, especially sensitive data, different authorizing rights are configured for sensitive data based on different user levels. For example, a user with a higher authorizing right can view some or all of the sensitive data; a user with a lower authorizing right cannot view the sensitive data, thereby effectively ensuring the privacy security of users.

According to various embodiments of the disclosure, any suitable techniques can be applied to data de-sensitization, without limitations, based on design requirements and application scenarios. For example, data encryption is performed on sensitive data to obtain encrypted sensitive data. For another example, sensitive data is converted into corresponding virtual information based on preset conversion rules. Such virtual information prevents sensitive data from disclosure and is identifiable by a respective data processing apparatus. In other words, sensitive data can be de-sensitized in any manner, as long as the data desensitization operation is performed on sensitive data.

Figure 8:
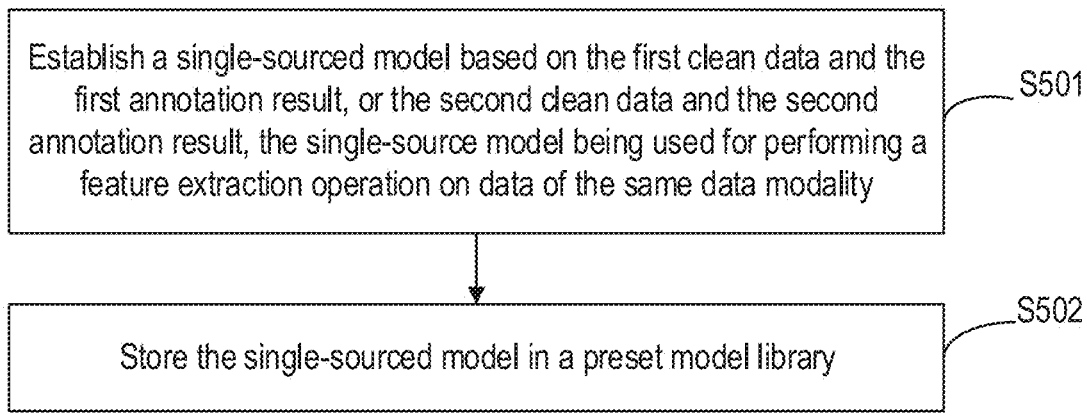
FIG. 8 is a flow diagram illustrating a data processing method according to some embodiments of the disclosure.

FIG. 8 is a flow diagram illustrating a data processing according to some embodiments of the disclosure. As shown in FIG. 8, and based on the above-described embodiments, to improve its practical applications, the method further includes the following step.

Step S501: establish a single-sourced model based on the first clean data and the first annotation result, or the second clean data and the second annotation result, the single-sourced model being used for performing a feature extraction operation on data of the same modality.

The single-sourced model is obtained by modeling data of only a single modality (e.g., the first clean data and the first annotation result, or the second clean data and the second annotation result), or data of various portions subdivided in the same modality. A single-sourced model is configured to learn characteristics of the data, and extract basic features and representative features of such data. Basic features includes, for example, at least one of the following: attribute information included in the data itself, and shallow description of the data obtained based on classic methods. For instance, attribute information includes intrinsic characteristics of data, such as the body parts, department, gender, age, region, types of disease, and the like. These characteristics are stored in an encoded mode to capture features understandable by a computer.

The shallow description information is the shallow information extracted from data using, for example, the algorithms with mature applications. Using an image as an example, features (e.g., color, shape, texture, and region) of the image is extracted using the description operators such as a scale-invariant feature transform (SIFT) algorithm, a histogram of oriented gradients (HoG) algorithm, a Laplacian of Gaussian (LoG) algorithm, and a Gabor algorithm. Further, the representative features are inherent and hidden abstract features of the data learned via modeling the data using machine learning and deep learning technologies. In one example, the representative features include at least one of the following: deep feature graph(s) of a deep neural network (DNN), or feature vector(s) of a DNN.

Step S502: store the single-sourced model in a pre-configured model library.

After the single-sourced model is established, to facilitate applications of the single-sourced model, the established single-sourced model is stored in a preset model library.

In some embodiments, after the single-sourced model is established, to improve the accuracy of feature extraction performed by the single-sourced model, the single-sourced model is trained and optimized, using structured multi-modal data stored in a database, until the model converges and the performance satisfies the actual application requirements. Afterward, the optimized single-sourced model is packaged and stored in the model library, with API interface(s) provided for invocation by management and/or analysis modules, subsequently. In one example, since the data processed by a processing apparatus is data of different singular modalities, data of different modalities invokes different single-sourced models in different application scenarios. As such, a model selection algorithm is pre-configured so that data and its respective processing model is adaptively matched via the model selection algorithm.

Figure 9:
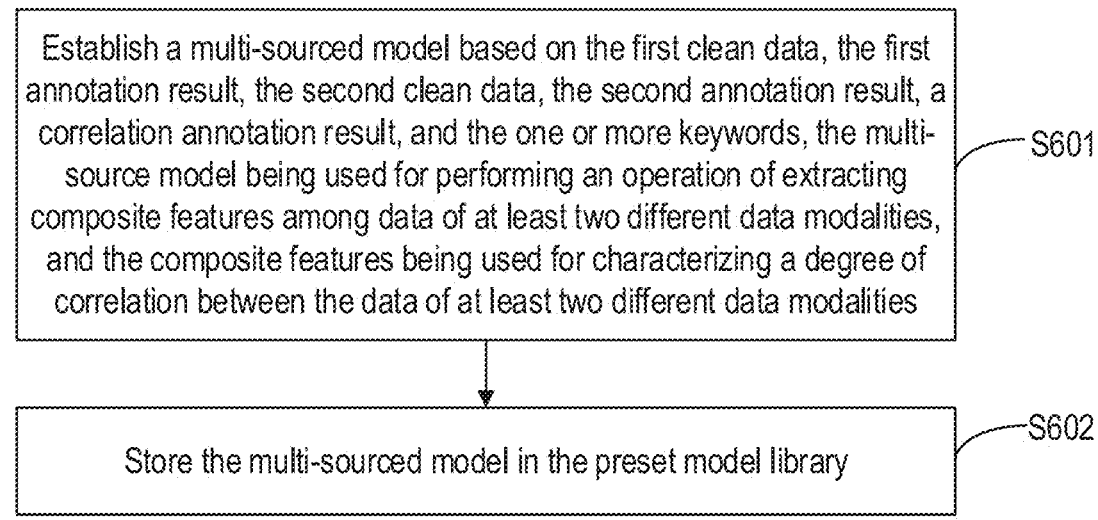
FIG. 9 is a flow diagram illustrating a data processing method according to some embodiments of the disclosure.

FIG. 9 is a flow diagram illustrating a data processing method according to some embodiments of the disclosure. As shown in FIG. 9, and based on the above-described embodiments, to improve the practical applications, the method further includes the following steps.

S601: establish a multi-sourced model based on the first clean data, the first annotation result, the second clean data, the second annotation result, a correlation annotation result, and the correlating keyword(s). The multi-sourced model being used for performing an operation to extract composite features associated with data of at least two different data modalities, and the composite features being used for characterizing a degree of correlation between the data of at least two different data modalities.

In some embodiments, the multi-sourced model is a model algorithm obtained by learning and training simultaneously with data of a plurality of modalities (e.g., the first clean data, the first annotation result, the second clean data, the second annotation result, the correlation annotation result, and the correlating keyword(s)). Afterwards, when data of the plurality of modalities is analyzed using the multi-sourced model, the commonalities in such data of different modalities are automatically identified, thereby finding hidden connections, and extracting more complex features (referred to as composite features). For example, in the case of complex application scenarios in the medical field, multi-sourced data analysis is common. For instance, there are a CT image and an MRI image of the same foci, CT images of the same patient in different periods, a combination of an image and a medical record report, and information of pharmaceutical molecules in connection with a pathological section slides. Thus, a multi-sourced model often renders better performance than a single-sourced model.

Step S602: store the multi-sourced model in the pre-configured model library.

After the multi-sourced model is established, to facilitate applications of the multi-sourced model, the established multi-sourced model is stored in the pre-configured model library.

According to various embodiments, after the multi-sourced model is established, to improve the accuracy of feature extraction by the multi-sourced model, the multi-sourced model is trained and optimized with structured multi-modal data in a database until the model converges and its performance satisfies actual application requirements. Afterwards, the optimized multi-sourced model is packaged and stored in the model library, with API interface(s) provided for invocation by management and/or analysis modules, subsequently. In some embodiments, since data processable by a processing apparatus is multi-modal data, different models are invoked for data of different modalities and in different application scenarios. Therefore, a model selection algorithm is pre-configured such that data and a corresponding model is adaptively matched via the model selection algorithm. For example, when the data is single-sourced data, the single-sourced model is used for processing; when the data is multi-sourced data, the multi-source model is used for processing.

Figure 10:
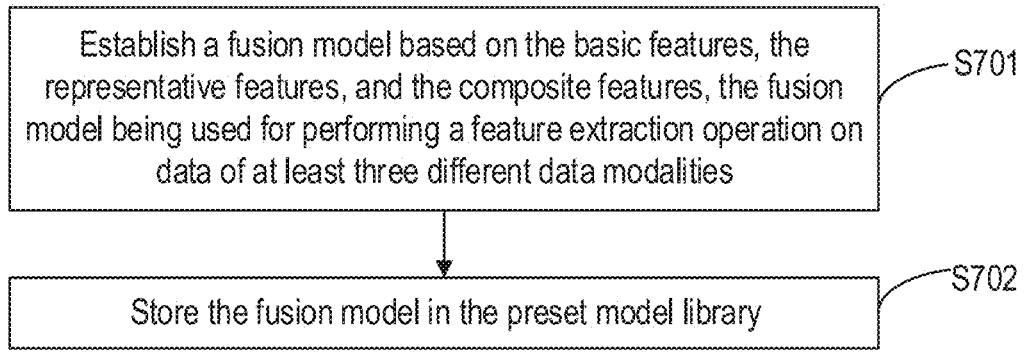
FIG. 10 is a flow diagram illustrating a data processing method according to some embodiments of the disclosure.

FIG. 10 is a flow illustrating a data processing method according to some embodiments of the disclosure. As shown in FIG. 10, and based on the above-described embodiments, to improve the practical application, the method further includes the following steps.

Step S701: establish a fusion model based on the basic features, the representative features, and the composite features, the fusion model being used to extract composite features among data of at least three different data modalities.

After the basic features, the representative features, and the composite features are obtained, the basic features, the representative features, and the composite features is used for learning and training such that to establish a fusion model. Since the composite features reflect correlating relationship(s) between data of at least two different data modalities, and the basic features and the representative features reflect data features of one data modality, after the fusion model is established based on the composite features, the basic features, and the representative features, the fusion model is used to extract fusion features of data of at least three different modalities. Therefore, when data of different modalities is analyzed using the fusion model, analytical processing is performed on more complex data such as omic analysis to extract features with stronger characterizations, thereby meeting data analysis requirements of users.

Step S702: store the fusion model in the pre-configured model library.

After the fusion model is established, to facilitate applications of the fusion model, the established fusion model is stored in the pre-configured model library.

According to various embodiments, after the fusion model is established, to improve the accuracy of feature extraction by the fusion model, the fusion model is trained and optimized with structured multi-modal data in a database until the model converges and its performance meets actual application requirements. Afterwards, the optimized fusion model is packaged and stored in the model library, with API interface(s) provided for invocation by management and/or analysis modules, subsequently. In some embodiments, since data processable by a processing apparatus is multi-modal data, different models are invoked for data of different modalities and in different application scenarios. As such, a model selection algorithm is pre-configured so that data and a corresponding processing model is adaptively matched via the model selection algorithm. For example, when the is single-sourced data, the single-sourced model is used for processing; when the data is multi-sourced data, the multi-sourced model is used for processing; when the data is more complex multi-sourced data, the fusion model is used for processing.

Figure 11:
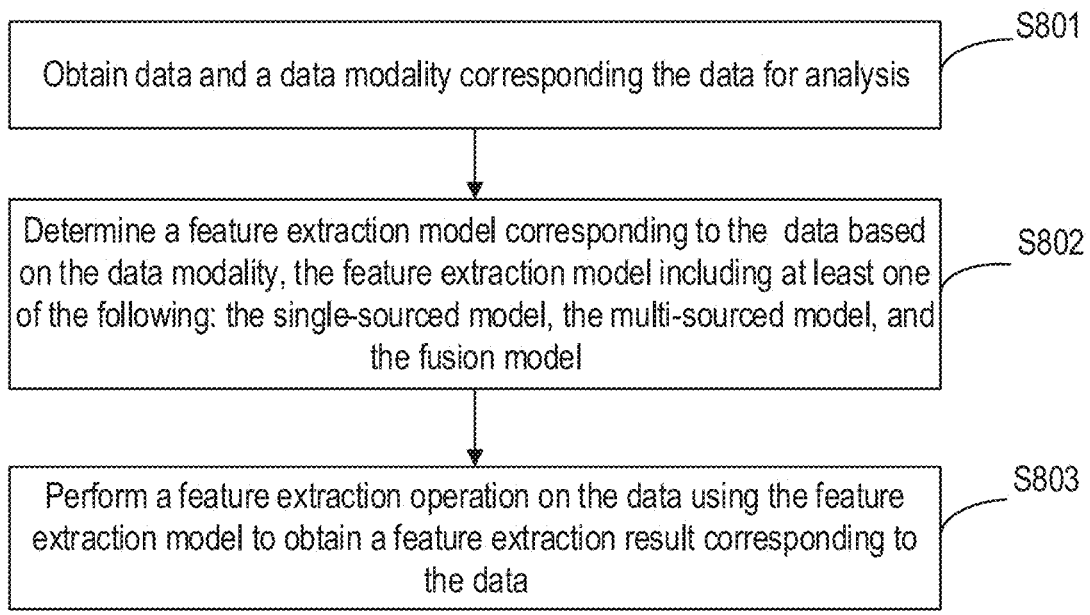
FIG. 11 is a flow diagram illustrating a data processing method according to some embodiments of the disclosure.

FIG. 11 is a flow diagram illustrating a data processing method according to some embodiments of the disclosure. As shown in FIG. 11, and based on the above-described embodiments, the method further includes the following steps.

Step S801: obtain data and a data modality corresponding to the data.

In some embodiments, the data includes data requiring a feature extraction operation. For example, it is single-sourced modal data, or multi-sourced modal data. Since data of different modalities corresponds to different data processing models, after the data is obtained, a data modality of the data is analyzed and identified to obtain a data modality corresponding to the data.

Step S802: determine a feature extraction model corresponding to the data based on the data modality, the feature extraction model including at least one of the following: a single-sourced model, a multi-sourced model, and a fusion model.

In some embodiments, after the data modality is obtained, a feature extraction model corresponding to the data is determined using a mapping relationship between data modalities and feature extraction models. For example, when the data is single-sourced modal data, a single-sourced model for analyzing the single-sourced modal data is determined. When the data is multi-sourced modal data, as the multi-sourced modal data is correlated data of a plurality of modalities, a multi-source model for analyzing the multi-source modal data is determined. When the data is complex multi-sourced modal data, a fusion model for analyzing the multi-sourced modal data is determined.

Step S803: perform a feature extraction operation on the data using the feature extraction model to obtain a feature extraction result corresponding to the data.

In some embodiments, after the feature extraction model is obtained, a feature extraction operation is performed on the data using the feature extraction model to obtain a feature extraction result corresponding to the data. For example, when the data is single-sourced modal data, feature extraction is performed on the single-sourced modal data using the single-sourced model to obtain a feature extraction result including basic features and representative features. When the data is multi-sourced modal data, feature extraction is performed on the multi-sourced modal data using the multi-sourced model to obtain a feature extraction result including a composite feature. When the data is complex multi-sourced modal data, feature extraction is performed on the multi-sourced modal data using the fusion model to obtain a feature extraction result including fused features.

In one embodiment, after obtaining the feature extraction result corresponding to the data, the method further includes a step S804 to encode the feature extraction result to obtain a feature search code corresponding to the feature extraction result.

After the feature extraction result is obtained, the feature extraction result is encoded based on pre-configured encoding rules such that a feature search code corresponding to the feature extraction result is obtained. The feature search code is used for accurate and effective data searches.

In one embodiment, after the data is obtained, a feature extraction model is determined based on a data modality type of the data. This way, an adaptive matching process is enabled between the data and the feature extraction model. A feature extraction operation is performed on the data using the determined feature extraction model, thereby ensuring the accuracy and reliability in obtaining the feature extraction result.

Figure 12:
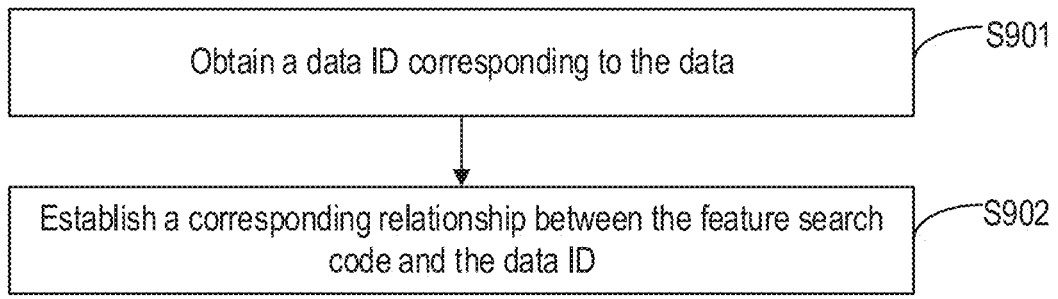
FIG. 12 is a flow diagram illustrating a data processing method according to some embodiments of the disclosure.

FIG. 12 is a flow illustrating a data processing method according to some embodiments of the disclosure. As shown in FIG. 12, and based on the above-described embodiments, after obtaining the feature search code corresponding to the feature extraction result, the method further includes the following steps.

Step S901: obtain a data ID corresponding to the data.

Step S902: establish a corresponding relationship between the feature search code and the data ID.

After the feature search code corresponding to the feature extraction result is obtained, to establish a corresponding relationship between the feature search code and the data, a pre-configured data ID corresponding to the data is obtained. A corresponding relationship is established between the feature search code and the data ID, improving the quality and efficiency of data retrieval.

Figure 13:
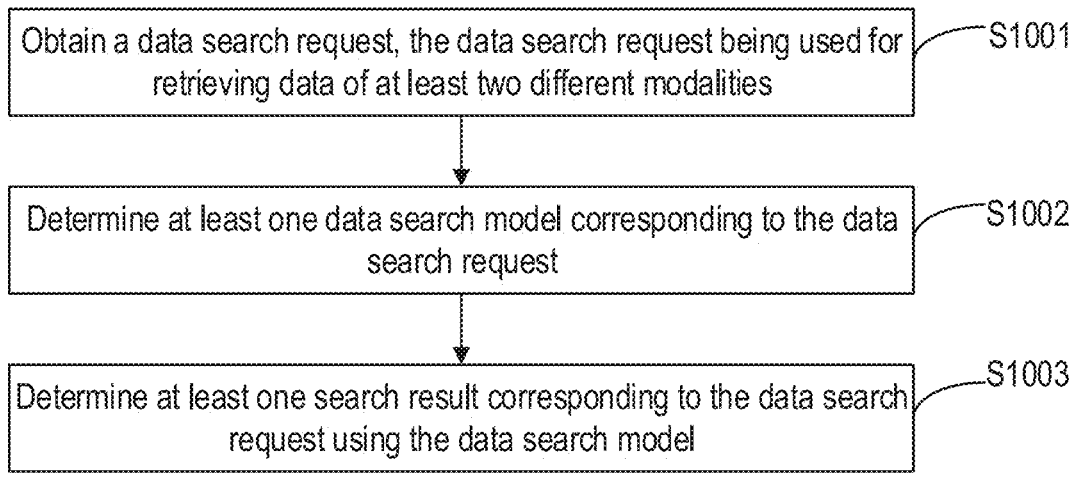
FIG. 13 is a flow diagram illustrating another data processing according to some embodiments of the disclosure.

FIG. 13 is a flow diagram illustrating another data processing method according to some embodiments of the disclosure. As shown in FIG. 13, a data processing method is executed by a data processing apparatus. In various embodiments, the processing apparatus is implemented as software, hardware, or a combination thereof. In one embodiment, the data processing method includes the following steps.

Step S1001: obtain a data search request, the data search request being used for performing data searches on data of at least two different modalities.

In some embodiments, the data search request is obtained based on an operation of a user. The data search request is for searches on data of at least two different modalities. For example, the data search request is to obtain medical data of a user A, while a database to be searched stores medical data of a plurality of users, with different medical data being separately stored. That is, the database stores data of at least two different modalities (e.g., medical image data, medical examination data, and medical report data). In this case, when a search is against the database, search data results (e.g., medical image data, medical examination data, and medical report data) of at least two different modalities corresponding to the data search request is obtained.

Step S1002: determine at least one data search model corresponding to the data search request.

After the data search request is obtained, at least one data search model for data search is determined based on the data search request. In this case, the data search model includes at least one of the following: a single-sourced model, a multi-sourced model, and a fusion model.

Step S1003: determine at least one search result corresponding to the data search request using the data search model.

After the data search model is obtained, a data search is performed using the data search model to obtain at least one search result corresponding to the data search request. For example, a data search request is to retrieve brain CT and lung CT data of a user A. For brain CT data, a brain single-sourced model for searching brain CT data is determined. For lung CT data, a lung single-sourced model for searching lung CT data is determined. That is, one data search request corresponds to one or more different single-sourced models. In another example, when the data search request is to retrieve lung CT image data and MRI image data of user A, a multi-sourced model corresponding to both CT image data and MRI image data is determined. A search is made in the database using the multi-sourced model to obtain at least one search result corresponding to the data search request. For another example, the data search request is to retrieve lung CT image data, MRI image data, and clinical medical record data of user A. A search is made against the database using a fusion model to obtain at least one search result corresponding to the data search request.

Figure 14A:
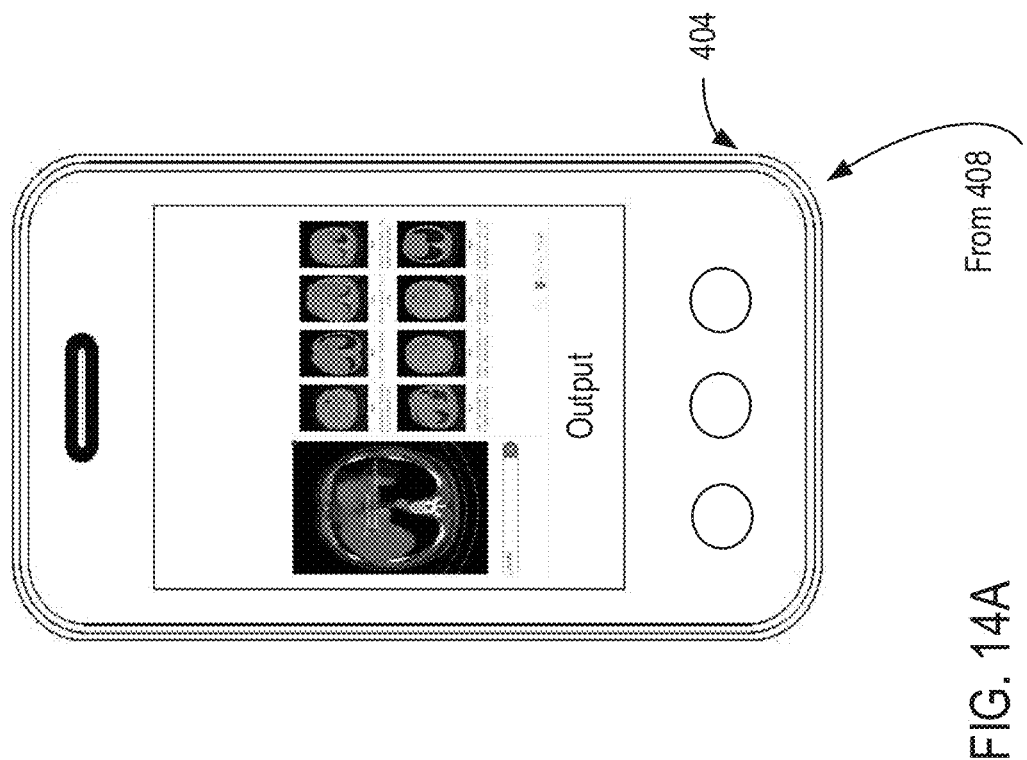
FIGS. 14A-B are schematic diagrams illustrating a method for sorting a plurality of search results according to some embodiments of the disclosure.

FIG. 14A is a diagram illustrating a data search on a client device (e.g., a mobile phone, a tablet computer, a desktop computer, or any other apparatus capable of data searches) according to some embodiments of the disclosure. When the data search request includes searches for data of at least one modality, the determining of at least one search result corresponding to the data search request using the data search model includes the following steps.

Step S10031: obtain a feature extraction model corresponding to the search data.

The search data of at least one modality includes data of any types of data modality. For example, the search data includes image data, report data, or the like. After the search data included in the data search request is obtained, to improve the accuracy and reliability of data searches, data feature information of the search data is extracted first. In some embodiments, first, the data modality corresponding to the search data is identified. Next, a feature extraction model (e.g., a feature extraction neural network) corresponding to the search data is obtained based on the data modality of the search data. In some embodiments, the feature extraction model includes at least one of the following: a single-sourced model, a multi-sourced model, and a fusion model. For example, the single-sourced model is used for performing a feature extraction operation on data of the same data modality; the multi-sourced model is used for performing a feature extraction operation on data of at least two different data modalities; and the fusion model is used for performing a feature extraction operation on data of at least three different data modalities.

According to various embodiments, the above-described feature extraction model is obtained by learning and training using data pre-stored in a database. Such data in the database includes data of different modalities stored in an associative manner based on one or more correlating keywords. For example, the data includes first data of a first data modality, and second data of a second data modality, and the first data and the second data correspond to a correlating keyword 1. This way, the first data and the second data is stored in the database based on the correlating keyword 1. Afterwards, the stored first data and second data is separately annotated to obtain a first annotation result and a second annotation result, respectively. A feature extraction model is established based on the first data and the first annotation result, and/or the second data and the second annotation result such that the feature extraction model is configured to perform a feature extraction operation for data of different modalities.

Step S10032: perform a feature extraction operation on the search data using the feature extraction model to obtain data feature information corresponding to the search data.

After the feature extraction model is obtained, a feature extraction operation is performed on the search data using the feature extraction model to obtain data feature information corresponding to the search data. Search data of different data modalities corresponds to different data feature information. For example, when the search data is image data of a single modality, a feature extraction operation is performed on the image data using the single-sourced model to obtain basic features and representative features corresponding to the image data. When the search data is CT image data and MRI image data that is in association, a feature extraction operation is performed on the search data using the multi-sourced model to obtain composite features corresponding to the CT image data and the MRI image data. When the search data is CT image data, MRI image data, and clinical medical record data that is in association, a feature extraction operation is performed on the search data using the fusion model to obtain fusion features corresponding to the search data.

Step S10033: determine at least one search result corresponding to the data search request using the data search model and the data feature information.

After the data feature information is obtained, a data search operation is performed using the data search model and the data feature information to obtain at least one search result corresponding to the data search request. This way, the accuracy and reliability of the search result. effectively ensured.

According to various embodiments, the at least one determined search result corresponding to the data search request changes as the searching time and the amount of data for searches change. In some embodiments, the at least one search result is pre-stored in a database; while data (including image data, text data, therapeutic schemes, drug instructions, and so on) in the database is updated periodically and/or in real time. In this case, the amount of data for searches in the database also increases with the update operations. For the same data search request, two different search results are obtained before and after the update operation is performed on the data in the database. In general, the search result obtained based on the database after the update operation is more accurate and reliable.

According to embodiments of the disclosure, data processing methods includes determining, based on a data search request at least one data search model corresponding to the data search request. Next, at least one search result corresponding to the data search request is determined using the data search model, the search result changes as the searching time and/or the amount of data for searches changes. This way, the accuracy of the search result is effectively improved, as a result of which the diagnosing and medical treatment skill level of medical workers is enhanced. In addition, different data search models are determined based on different data search requests such that the quality and efficiency of data searches using different data search models are improved, further improving the practical applications of the method, and facilitating market promotion and adoptions.

Figure 14A:
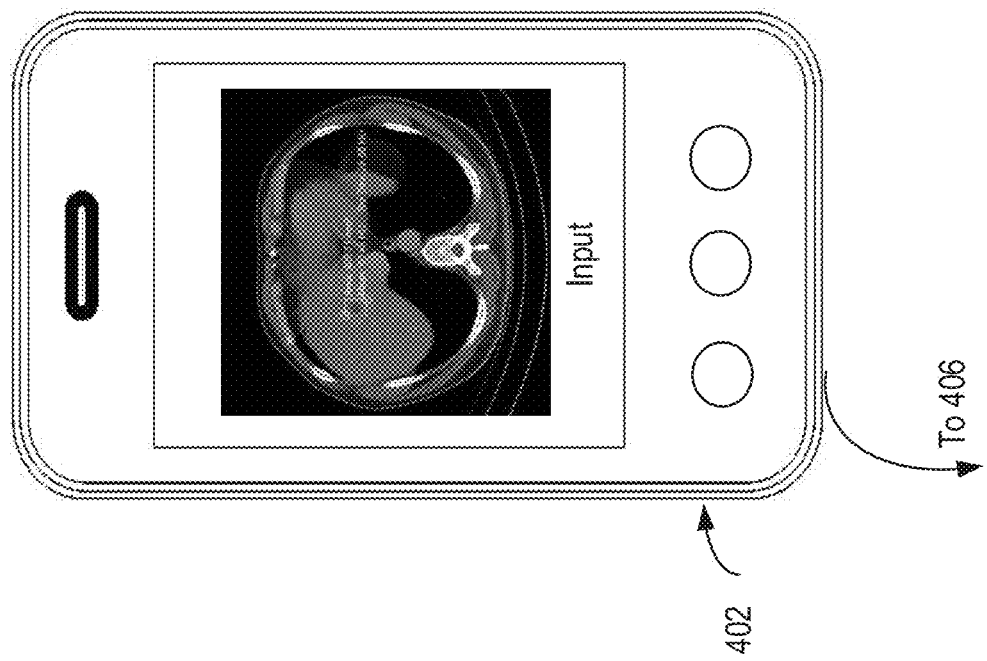

Further, as shown in FIG. 14, when a plurality of search results exist, the method further includes the following steps.

Step S1004: display the plurality of search results in a preset order.

In some embodiments, when a plurality of search results exist, the plurality of search results are sorted and displayed in a preset order. For example, the preset order is a preset displaying order. Any suitable ordering techniques can be applied, without limitations, based on application requirements. For instance, the preset order is related to the matching degree of the search results. In one example, the plurality of search results are displayed based on the matching degree in a descending order; or the matching degree in an ascending order. Further, probability information corresponding to the search results is also obtained. In one example, the probability information corresponding to the search results is determined based on the matching degree between the search results and search data. When the plurality of search results are displayed, a prompt of probability information is presented accordingly. For example, the probability information is presented to a user via voice announcement or textual display such that the user quickly and intuitively obtains relevant information of the search results.

Figure 14B:
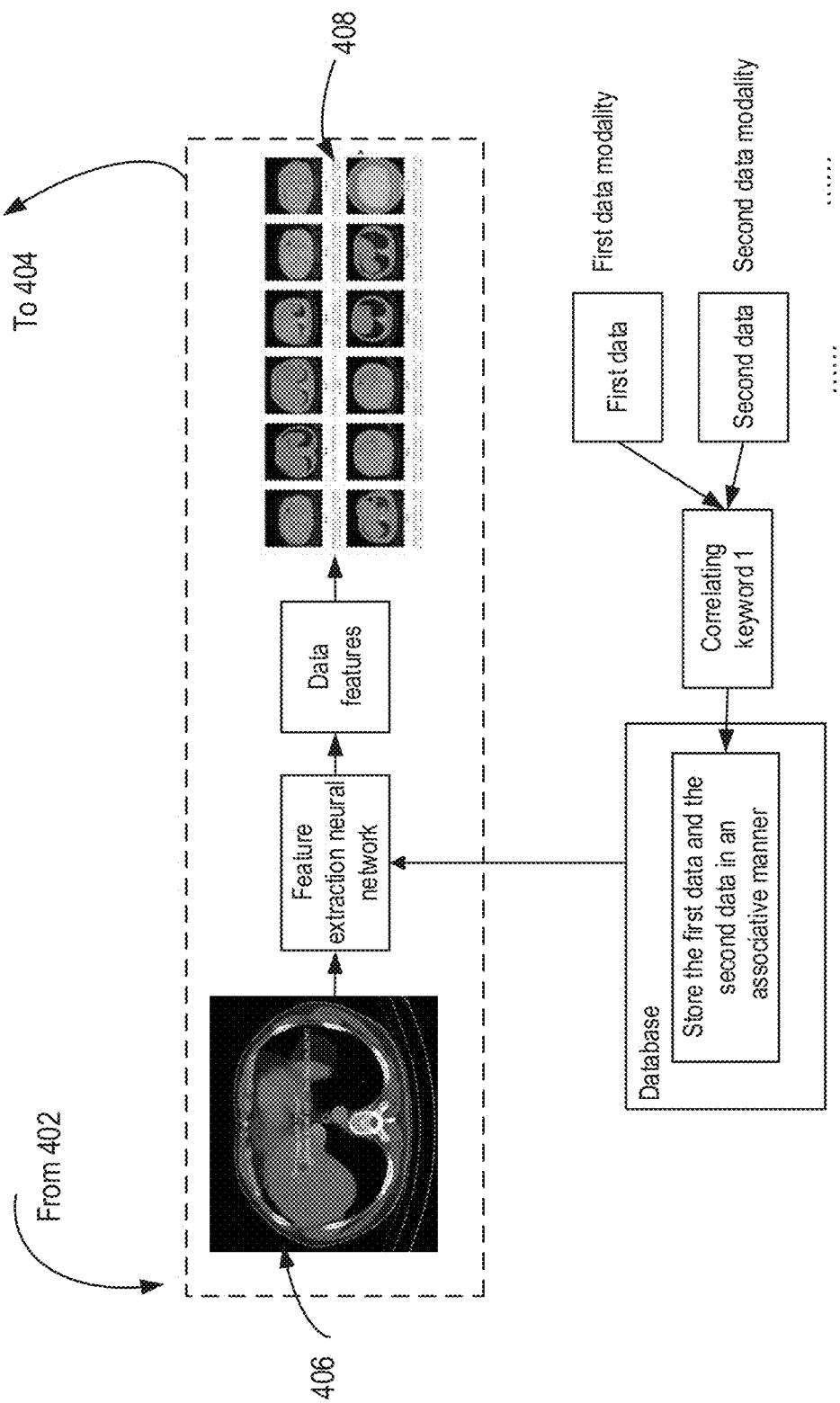

As shown in FIGS. 14A-B, for an item of basic image data, multiple reference image data similar to the basic image data is retrieved from the database. In this case, the multiple reference image data is displayed based on the correlating degree between the reference image data and the basic image data in a descending order. Alternatively, the multiple reference image data is displayed based on the correlation between reference foci information in the reference image data and the foci information in the basic image data, in a descending order.

According to various embodiments, a plurality of search results are displayed in a preset order such that a user can quickly and effectively obtain search results of a high matching degree. Further, it is convenient for the user to find the most qualified target search result from the plurality of search results, improving the quality and efficiency of data searches.

In some embodiments, based on the above-described embodiments, the method further includes the following steps.

Step S1101: perform data mining on the at least one search result to obtain an analysis result corresponding to the search result.

After the at least one search result is obtained, data analysis is performed based on the search result such that a user can better understand the data and explore the value of the data. The performing of data mining on the at least one search result includes at least one of the following: statistical analysis and reasoning analysis.

In some embodiments, a statistical analysis of the at least one search result includes performing simple statistics on the information in the search result based on the search result. In one example, a statistical result (e.g., a region distribution, age distribution, gender ratio, and survival time related to specific diseases) is obtained based on features of data. Such the statistical result provides guidance for users or other managing institutions. For instance, with statistics collected on the foci types in a search result based on a medical record report, probabilities of different diseases is obtained, assisting doctors in diagnosis. With statistics collected on treatment effects of different treatment plans based on follow-up records, feasible treatment plans are recommended to doctors and users.

Further, in some embodiments, the at least one search result is reasoned using a preset learning reasoning tool. In some embodiments, underlying knowledge is mined using similar search results obtained by a search with a data analysis model provided in a model library. For example, with correlation analysis, the commonalities and differences in different types of diseases are identified to help doctors learn about the illness. With time series analysis, manifestations of a disease are discovered in different periods such that medical workers can prescribe medications based on the illness and the manifestations of the disease in different periods. With omic analysis on a plurality of search results, a connection between such data is searched, based on the knowledge such as gene, protein, and pathology, to identify the cause, leading to new drug discoveries, new treatments, or the like, promoting the progress and development of medical technology.

According to various embodiments, to solve the defects in the current technologies (e.g., (a) occurrence of data chain breaking leading to multi-modal medical data not being structured for unified storage; (b) management and analysis of medical data is independent from each other, causing inefficient utilization of a large amount of medical data), a search and analysis system for fused multi-modal medical data is provided. The system is configured to connect the complete medical data chain, and perform structured unified storage and/or management on data of different modalities. Moreover, a plurality of types of machine learning models are constructed to perform modeling, feature extraction on the multi-modal data, and interfaces for interactive searches and automatic data analysis are designed based on professional medical background knowledge. As such, users can conveniently and accurately locate data of interest from the database, based on which further analysis and mining of the data is performed, helping the users better manage and understand the data.

Figure 15:
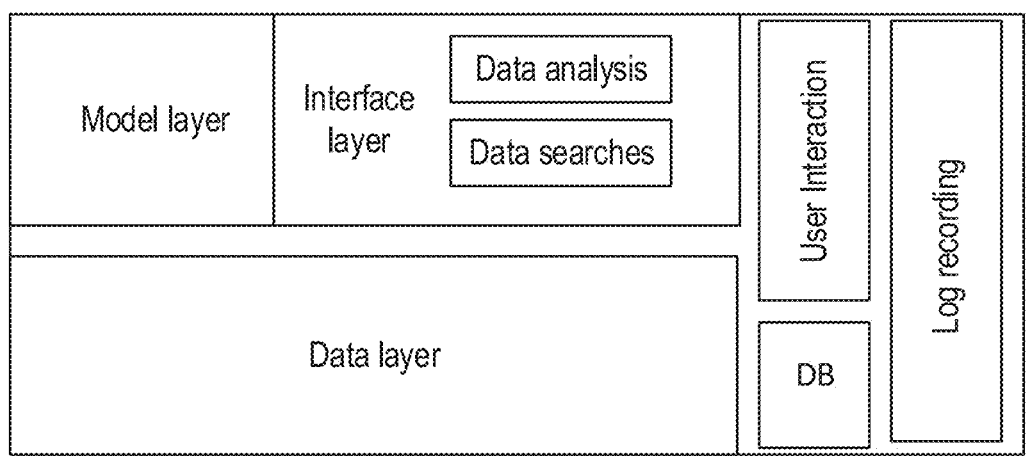
FIG. 15 is a block diagram illustrating a data processing apparatus according to some embodiments of the disclosure.

FIG. 15 is a block diagram illustrating an analysis system according to some embodiments of the disclosure. As shown herein, the analysis system includes: a data layer module, a model layer module, an interface layer module, a data storage module, a user interaction module layer, a log recording module, and so on. To perform the data processing method, one or more of: a data storage operation, a data modeling operation, a data search operation, and a data analysis operation are implemented. The following illustrates data processing process using an example in the field of healthcare.

Module 1: a data layer module configured to receive multi-modal medical data to structure medical data of different modalities, and to store the data in a database (DB) based on a pre-defined archiving protocol.

Since the medical data of different data modalities has no correlating relationship established, storage in associative manner cannot be implemented. In this case, one or more keywords correlating the medical data of different modalities are determined based on the pre-defined archiving protocol. The correlating keyword(s) reflect a correlating relationship between the medical data of different modalities. In some embodiments, the correlating keyword(s) include identity information of users, hospital information, medical consultation area information, or the like. The data of different modalities is stored in an associative manner based on the correlating keyword(s). In one embodiment, the storage of the multi-modal medical data includes the following steps.

Step 1: access data to obtain medical data from a HIS system or other data sources, and retrieve data of different modalities using a specially designed interface.

Step 2: inspect data quality for the retrieved data.

In some embodiments, with the unified evaluation criteria set based on medical guidelines and doctors' opinions, the quality of the data is graded, This way, qualified data from different sources is mutually recognized, and unqualified data is deleted. For example, for the same type of image data, the quality of obtained image data varies depending on how new or advanced an image device is. That is, both blurred image data and clear image data is obtained through different image devices. In this case, after the image data is analyzed using the evaluation criteria, the blurred image data is evaluated as unqualified data, and the clear image data is evaluated as qualified data. Alternatively, for data of a text type, if the content of the data is relatively complete, the data of the text type is evaluated as qualified data; otherwise, the data of the text type is evaluated as unqualified data.

Step 3: data de-sensitization.

In some embodiments, the data desensitization operation is an optional operation, depending on the actual application situation. When a user has a data de-sensitization need, private information such as patient information, doctor information, and hospital information in the data is deleted, replaced, or redacted based on relevant rules/regulations to achieve the effect of de-sensitization of the data.

Step 4: classify data, and clean the data based on a classification result.

Classifying and identifying qualified data is for selecting cleaning methods corresponding to different modalities in subsequent processing. The qualified data is cleaned using a cleaning method selected based on the classification result. In some embodiments, ambiguities in the qualified data is adjusted, via, for example, any one of the following operations: de-duplication, error correction, conversion, checking and adding of missing items, and the like. The qualified data is processed using the cleaning method to achieve consistency checks on the qualified data.

For example, for the existing CT image data and blood test data of the same patient, the age information of the patient is missing in the CT image data, but exists in the blood test data. Then, the field data related to the age information of the patient is added to the CT image data using the correlation of data, ensuring the consistency and integrity of the data.

Step 5: establish a data ID.

Unique ID information is assigned to each items of the data after cleaning. Further, the same correlation ID is assigned to correlated data to establish a connection. For example, a correlation ID is established for all data associated with the same keyword (user information, hospital information, region information, or the like).

Step 6: annotate data.

In some embodiments, the data annotation operation is an optional operation, depending on the application situation of data search and analysis. For example, data annotation includes foci annotation in an image, disease type annotation in a report, or extraction of indexed examination results. The data annotation operation extracts the key portion(s) in the data. According to some embodiments, the operation of data annotation is mainly performed for image data. For example, an annotation operation is performed on the foci information in image data. The foci information includes at least one of the following: a foci type, foci location, foci size, and foci shape. Annotations are also performed for the correlation and/or similarity between two pieces of image data to facilitate searches of the data based on annotation results, improving the precision of data searches.

Step 7: store the data in structured manner.

Processed data is stored in a secure, flexible, and efficient database (DB) based on a pre-defined archiving protocol (e.g., field definitions in a file header). In some embodiments, the archiving protocol is provided with correlating keyword(s) for storing data such that the data of at least two different modalities is stored in an associative manner based on the correlating keyword(s).

Module 2: a model layer module configured to establish corresponding machine learning models based on the data types of different modalities and different usage scenarios. The models are trained and optimized using structured data in the database. The optimized models are stored in a model library, which are used to extract features of corresponding data to form a feature set. Such feature set is further stored in a feature database to provide the underlying algorithm support for interface(s) for subsequent data searches and analysis. In some embodiments, three types of feature extraction models are established based on the characteristics of multi-modal data: a single-sourced model, a multi-sourced model, and a multi-feature fusion model.

Figure 16:
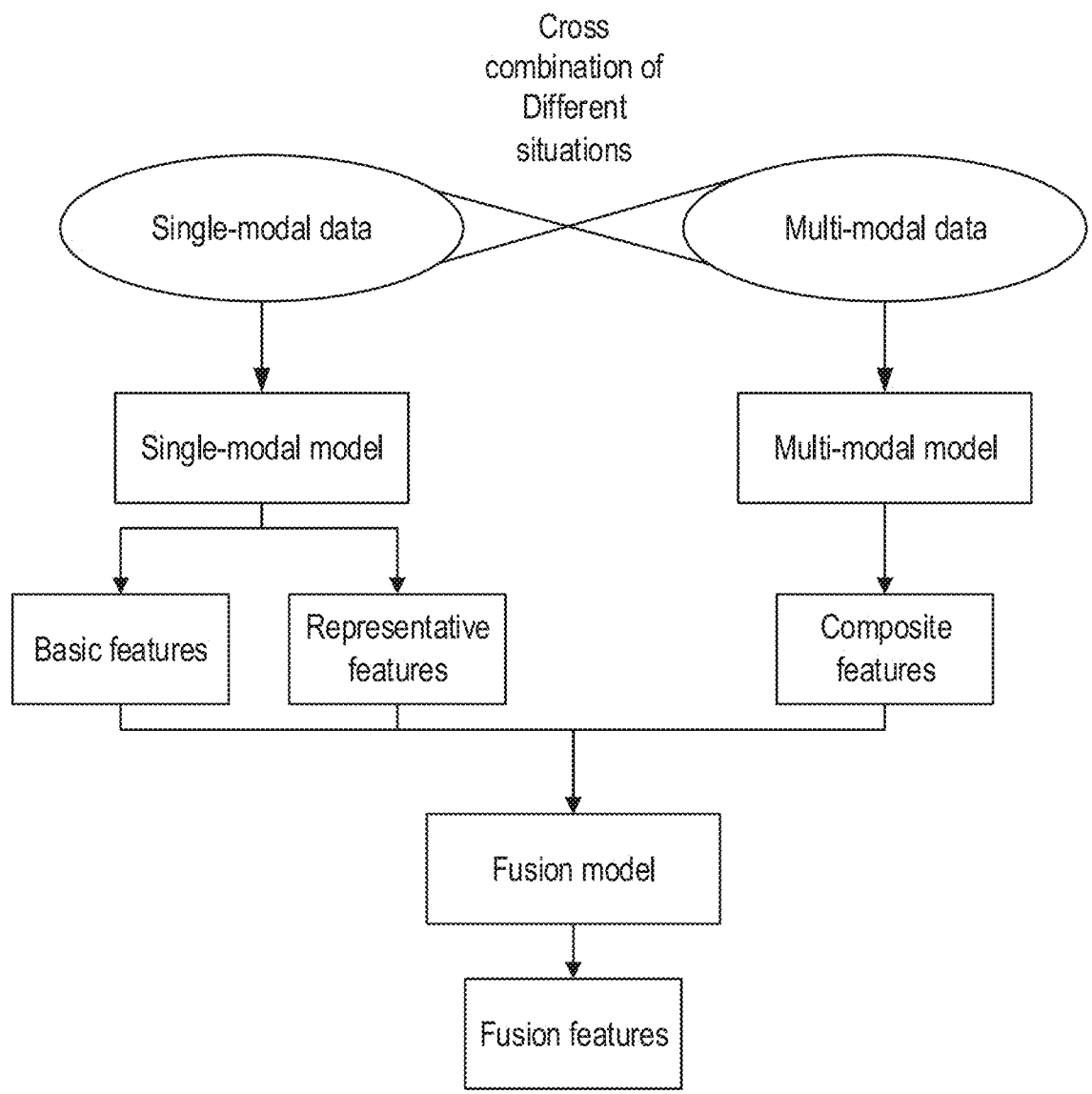
FIG. 16 is a schematic diagram illustrating a method for establishing a data search model according to some embodiments of the disclosure.

Referring now to FIG. 16, a flow diagram illustrating a method for data modeling according to some embodiments of the disclosure. As shown in FIG. 16, the method includes the following steps.

Step 11: obtain data of a specific data modality and an annotation result corresponding to the data.

Step 12: establish a single-sourced model based on the data and the annotation result, the single-sourced model being used for performing a feature extraction operation on data of the same data modality.

Step 13: store the single-sourced model in a preset model library.

In some embodiments, the single-sourced model is obtained by modeling data of only one modality or data of various portions subdivided in the same modality. The single-sourced model learns the characteristics of such data, and extract basic features and representative features of such data.

Step 21: obtain data of at least two different data modalities and an annotation result corresponding to the data.

Here, a cross combination of single-modal data results in multi-modal data. For example, data of at least two different data modalities is formed by cross-combining at least two types of different single-modal data.

Step 22: establish a multi-sourced model based on the data and the annotation result, the multi-sourced model being used for performing a feature extraction operation on the data of at least two different data modalities.

Step 23: store the multi-source model in the preset model library.

In some embodiments, the multi-sourced model extracts composite features among the data of at least two different data modalities. For complex application scenarios in the medical field, analysis of multi-sourced data is common: for example, there are a CT image and an MRI image having the same foci information, CT images of the same patient in different periods, a combination of an image and a medical record report, and information of pharmaceutical molecules in connection with a pathological section slides. Thus, the multi-sourced model often has better performance than the single-sourced model.

Step 31: basic features, representative features, and composite features is obtained for the data of at least two different data modalities based on the single-sourced model and the multi-sourced model.

Step 32: establish a fusion model based on the basic features, the representative features, and the composite features, the fusion model being used for performing a feature extraction operation among data of at least three different data modalities.

Step 33: store the fusion model in the preset model library.

In some embodiments, the multi-feature fusion model is used in more complex situations such as omic analysis to implement further analysis based on the features extracted by the single-sourced model and the multi-sourced model, correlate more features, and explore connections between various data. This way, features with stronger characterizations are extracted to meet data analysis requirements of users.

In some embodiments, single-modal data is analyzed using the single-sourced model. Multi-modal data is analyzed using the multi-sourced model and/or the fusion model. When the multi-modal data is analyzed using the multi-sourced model, if an analytical result does not meet requirements of a user, the fusion model is selected to perform analysis on the data. For example, in data searches, if the data to be searched is brain CT data, a data search is performed using the single-sourced model for brain CT searches. If the data to be searched is lung CT data, a data search is performed using the single-sourced model for lung CT searches. If the data to be searched includes lung CT image data and MRI image data, a data search is performed using the multi-sourced model. If the data to be searched includes lung CT image data, MRI image data, and clinical medical record data, a data search is performed using the fusion model.

Step 41: optimize the models and package the models.

The above-described three types of feature extraction models are trained and optimized using structured multi-modal data in a database until the models converge and the performance meets actual application requirements. The optimized feature extraction models are packaged and stored in the model library, with API(s) provided for invocation by management and/or analysis modules, subsequently.

In addition, feature extraction performed on the data based on the established model includes the following steps.

Step 51: read data and annotation information thereof in batches from the database.

In some embodiments, reading the data in batches is mainly dictated by the performance of memory and the processing apparatus. This way, the reading quality and efficiency of the data is ensured.

Step 52: select a corresponding feature extraction model for each item of data in the batches.

In some embodiments, one or more feature extraction models are selected. A feature extraction operation is performed on the data using the selected feature extraction model(s) to obtain a feature vector (e.g., vectors of integral numbers, real numbers, or Boolean typed variable) with a corresponding length of d (e.g., preset length). When a plurality of feature extraction models are selected, the plurality of feature extraction models perform feature extraction operations at the same time to effectively improve the efficiency of feature extraction.

Step 53: assign a search code UID to extracted features, the search code UID having a corresponding relationship with an ID of the original data. Next, the features are serialized into a database for invocation by management and/or analysis modules, subsequently.

Step 54: update features.

The feature extraction models in the model library are continuously updated and optimized. To ensure the accuracy of feature extraction, when the feature extraction models in the model library are updated, the features extracted using the original models in the feature database also need to be updated. In one example, feature extraction is performed again using the updated feature extraction models, and the original features in the database are overwritten using the same UID.

Module 3: an interface layer module configured to provide at least two functions including data searches and data analysis. When data searches are required, the interface layer module provides a plurality of interaction modes such that a user can quickly and accurately locate desired data from the database, and perform management operations (e.g., addition, deletion, searches, modification, and exportation) thereon. Data analysis is performed to further analyze retrieved multi-modal medical data based on a search result to help the user better understand the data and explore the value thereof. According to various embodiments, different analysis methods are applied for different application requirements.

In some embodiments, exemplary interaction modes provided by the interface layer module support, but are not limited to, the following functionalities.

1) Text field filtering, by which the user selects a specific text field, such as, time, gender, or body part, for searches.
2) Image searches, by which searches of medical images of different body parts and different modalities, as well as full-image searches and region of interest (e.g., foci) searches. In one example, the user uploads an image, and the backend of the analysis system automatically determines an image type and a pertinent body part. Further, it provides automatic detection of a focus, gauges the user's intention, and searches the database for similar images and corresponding reports and medical records (if any) thereof for returning to the user.
3) Report searches, by which the user inputs keywords, report fragments and complete reports. The backend extracts key information from the user input, searches the database for similar reports and corresponding images and medical records (if any) thereof for simultaneously returning to the user.
4) Medical record retrieval, by which the user inputs a medical record report, and the backend automatically identifies the disease, searches the database for similar medical records and corresponding images and reports (if any) thereof for returning to the user, and attaches corresponding treatment plans (if any recorded).
5) Disease searches, by which the user directly searches for a disease name. The backend searches the database for all the data related to the disease including images, reports, medical records, and treatment plans (if any) for returning to the user.
6) Foci searches, by which the user inputs a focus name. The backend directly returns images containing the focus and corresponding reports such that the user can more intuitively and comprehensively learn about the focus, including image manifestations and different diseases with the same symptoms.
7) Interactive searches, by which the user uses multi-modal data in searches. For example, for a search for an image plus a report, the backend automatically invokes a multi-sourced model for processing to return a more accurate searches result to the user.

According to various embodiments, different search modes correspond to different data search models. Moreover, in addition to the support of different search modes, fine sorting of search results is also supported. For example, the obtained search results include multi-modal data of both an image and a report. Any fine sorting rules are applied, without limitation. In one example, the fine sorting can be based on a degree of correlation between the search results and a degree of manual intervention. For instance, further fine sorting is performed on the search results based on relevant medical knowledge and user requirements (e.g., benign or malignant, grading of such benignness or malignancy vascular arborization, and organ segmentation and paganization) to meet the user's needs and quickly locate data of interest.

Module 4: a user interaction module, which is an extension to the interface layer. It encapsulates the functions of the interface layer into easy-to-use and user-friendly user interaction interface(s) to support visualization of the search results, analysis results, and other tools.

Module 5: a log recording module configured to record all operations of the above-described modules, monitor the operating status, resource consumption, and health status of each module, detect and warns for the working status of the system, and in case of faults, help the operation and maintenance locate a point of faults in time, perform emergency measures to quickly recover the functions of the entire system.

In some embodiments, faults occurring in the system relate to operations such as system outage, content beyond the scope, faults in the system operating status, errors of a software algorithm, a data size exceeding the standard, and the like. When a fault occurs in the system, a warning operation is performed so that the user can correct it in time.

Further, in some embodiments, data analysis performed on a search result using a model includes the following steps.

Step 61: perform statistical analysis

In some embodiments, simple statistics are performed on the information in the search result using a preset statistical analysis tool. For example, a region distribution, age distribution, gender ratio, survival time related with a specific disease, and the like are statistically obtained based on attribute features of data. Thus, guidance is provided for decision support of managing institutions. With statistics collected on foci types in the provide result based on a medical record report, probabilities of different diseases is obtained, assisting doctors in diagnosis. With statistics collected on treatment effects of different treatment plans through follow-up records, feasible treatment plans are recommended to doctors and users.

Step 62: reasoning analysis

In some embodiments, underlying knowledge in the search result obtained by searches is mined using a data analysis model provided in a model library. For example, with correlation analysis, the commonalities and differences in different types of diseases are identified to help doctors learn about the illness. With time series analysis, manifestations of a disease are discovered in different periods such that medical workers can prescribe medications based on the illness and the manifestations of the disease in different periods. With omic analysis on a plurality of search results, a connection between such data is searched, based on the knowledge such as gene, protein, and pathology, to identify the cause, leading to new drug discoveries, and/or new treatments.

With the search and analysis system provided in embodiments of the disclosure a complete medical data chain is connected, and structured unified storage and management is performed on data of different modalities. Moreover, a plurality of types of machine learning models are constructed to perform modeling and feature extraction on multi-modal data, and design interfaces for applications such as interactive searches and automatic data analysis based on professional medical background knowledge. As such, the user can conveniently find data of interest from the database, further analyze and mine the data, thereby better managing and understanding the data, and promoting the progress and development of medical technology.

Figure 17:
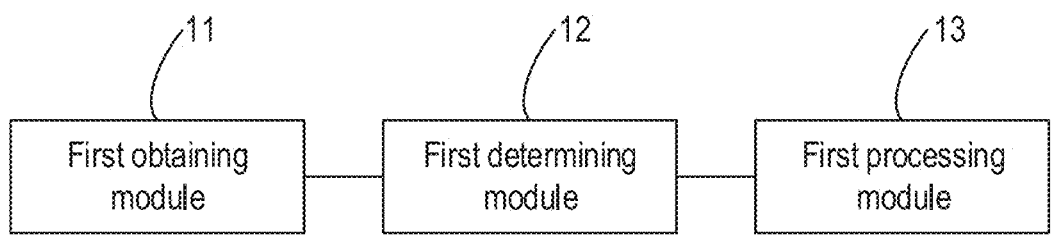
FIG. 17 is a block diagram illustrating a data processing apparatus according to some embodiments of the disclosure.

FIG. 17 is a block diagram illustrating a data processing apparatus according to some embodiments of the disclosure. In various embodiments, the data processing apparatus is configured to perform the above-described data processing methods. In some embodiments and as shown in FIG. 17, the apparatus includes: a first obtaining module (11), a first determining module (12), and a first processing module (13).

The first obtaining module (11) is configured to obtain data of at least two different modalities for processing, the data including at least first data and second data.

The first determining module (12) is configured to determine one or more keywords correlating the first data and the second data; and The first processing module (13) is configured to store the first data and the second data in an associative manner based on the one or more keywords.

In some embodiments, before storing the first data and the second data in an associative manner based on the one or more c keywords, the first obtaining module (11) and the first processing module (13) in are further configured as the following.

The first obtaining module (11) is further configured to obtain inspection criteria for quality inspection on the first data and the second data.

The first processing module (13) is further configured to separately perform quality inspection on the first data and the second data based on the inspection criteria.

In some embodiments, when separately performing quality inspection on the first data and the second data based on the inspection criteria, the first processing module (13) is further configured to: determine that the first data and/or second data is qualified data when the first data and/or second data meets the inspection criteria; or determine that the first data and/or second data is unqualified data when the first data and/or second data does not meet the inspection criteria.

In some embodiments, the first processing module (13) is further configured to: upon determining that at least one of the first data and the second data is unqualified data, delete the unqualified data; or upon determining that the first data and the second data are both qualified data, store the first data and the second data in an associative manner based on the one or more keywords.

In some embodiments, when storing the first data and the second data in an associative manner based on the one or more keywords, the first processing module (13) is further configured to: obtain first clean data corresponding to the first data and second clean data corresponding to the second data; and store the first clean data and the second clean data in an associative manner based on the one or more keyword.

In some embodiments, when obtaining first clean data corresponding to the first data and second clean data corresponding to the second data, the first processing module (13) is further configured to: obtain a first data modality corresponding to the first data and a second data modality corresponding to the second data; determine a first cleaning method for a consistency check on the first data based on the first data modality; determine a second cleaning method for a consistency check on the second data based on the second data modality; process the first data using the first cleaning method to obtain the first clean data; and process the second data using the second cleaning method to obtain the second clean data.

In some embodiments after storing the first data and the second data in an associative manner based on the one or more keywords, the first processing module (13) is further configured to: annotate the first data to obtain a first annotation result; annotate the second data to obtain a second annotation result; and perform correlation annotation on the first data and the second data to obtain annotated correlation information.

In some embodiments, the first processing module (13) is further configured to: establish a first data ID for the first data; establish a second data ID for the second data; and establish a correlation ID for the first data and the second data based on the one or more correlating keywords.

In some embodiments, the first processing module (13) is further configured to: obtain a data de-sensitization request for the first data and the second data; determine sensitive data corresponding to the data de-sensitization request in the first data and the second data; and perform data de-sensitization on the sensitive data.

In some embodiments, the first processing module (13) is further configured to: establish a single-sourced model based on the first clean data and the first annotation result, or the second clean data and the second annotation result, the single-sourced model being used for performing a feature extraction operation on data of the same data modality; and store the single-sourced model in a preset model library.

Features extracted by the single-sourced model for the data of the same data modality include at least one of the following: basic features and representative features. The basic features include, for example, at least one of the following: data attribute information, and data description information. The representative features include, for example, at least one of the following: a feature graph, and a feature vector.

In some embodiments, the first processing module (13) is further configured to: establish a multi-sourced model based on the first clean data, the first annotation result, the second clean data, the second annotation result, a correlation annotation result, and the one or more keywords, the multi-source model being used for performing an operation of extracting composite features among data of at least two different data modalities, and the composite features being used for characterizing a degree of correlation between the data of at least two different data modalities; and store the multi-sourced model in the preset model library.

In some embodiments, the first processing module (13) is further configured to: establish a fusion model based on the basic features, the representative features, and the composite features, the fusion model being used for performing a feature extraction operation on data of at least three different data modalities; and store the fusion model in the preset model library.

In some embodiments, the first obtaining module (11) and the first processing module (13) are further configured as the following.

The first obtaining module (11) is further configured to obtain data and a data modality corresponding to the data for analysis.

The first processing module (13) is further configured to determine a feature extraction model corresponding to the data based on the data modality, the feature extraction model including at least one of the following: the single-sourced model, the multi-sourced model, and the fusion model; and perform a feature extraction operation on the data using the feature extraction model to obtain a feature extraction result corresponding to the data.

In some embodiments, after obtaining the feature extraction result corresponding to the data, the first processing module (13) is further be configured to: encode the feature extraction result to obtain a feature search code corresponding to the feature extraction result.

In some embodiments, after obtaining the feature search code corresponding to the feature extraction result, the first obtaining module (11) and the first processing module (13) are further configured as the following.

The first obtaining module (11) is further configured to obtain a data ID corresponding to the data.

The first processing module (13) is further configured to establish a corresponding relationship between the feature search code and the data ID.

According to various embodiments, the apparatus of FIG. 17 is configured to perform the methods of FIG. 1 to FIG. 12 and FIG. 14 to FIG. 16. Details illustrated with references to FIG. 1 to FIG. 12 and FIG. 14 to FIG. 16 are not repeated.

Figure 18:
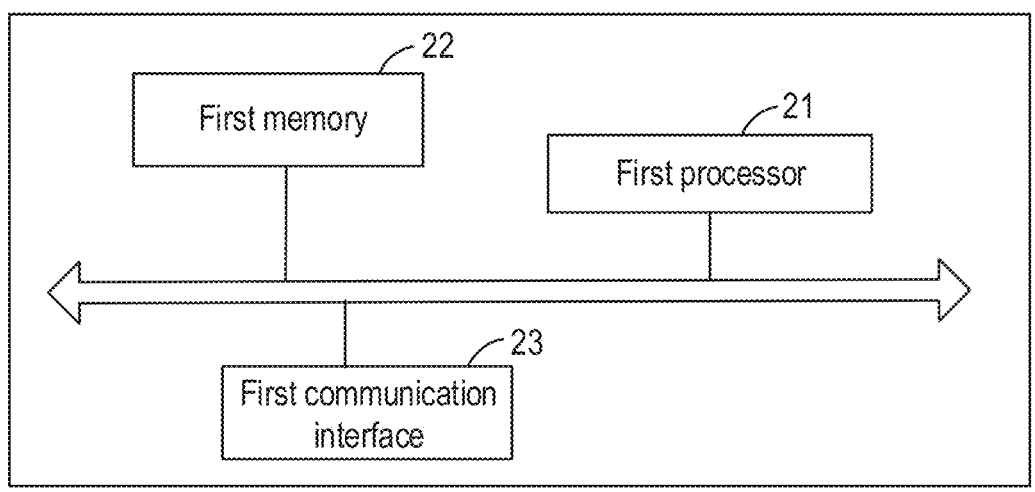
FIG. 18 is a block diagram illustrating an electronic device corresponding to the data processing apparatus of FIG. 17 according to some embodiments of the disclosure.

FIG. 17 is a block diagram illustrating an electronic device, according to some embodiments of the disclosure. In some embodiments, the electronic device is configured to implement the apparatus of FIG. 17. In some embodiments, the electronic device is a mobile phone, a tablet computer, a server, or the like. In one embodiment, and as shown in FIG. 18, the electronic device includes a first processor (21) and a first memory (22). The first memory (22) is configured to store a program that, when executed, instructs the electronic device to perform the data processing method provided in the embodiments of FIG. 1 to FIG. 12 and FIG. 14 to FIG. 16. The first processor (21) is configured to execute the program stored in the first memory (22).

The program includes one or a plurality of computer instructions, which, when executed by the first processor (21), implement the following steps.

Step 1: obtaining data of at least two different modalities for processing, the including at least first data and second data.

Step 2: determining one or more correlating keywords correlating the first data and the second data.

Step 3: storing the first data and the second data in an associative manner based on the one or more correlating keywords.

In some embodiments, the first processor (21) is further configured to perform all or some steps of the methods of FIG. 1 to FIG. 12 and FIG. 14 to FIG. 16.

In some embodiments, the electronic device further includes a first communication interface (23) for communicating with other devices or communication networks.

Further, embodiments of the disclosure provide a computer storage medium for storing computer software instructions executed by an electronic device, the computer storage medium including a program for performing the data processing method in the methods of FIG. 1 to FIG. 12 and FIG. 14 to FIG. 16.

Figure 19:
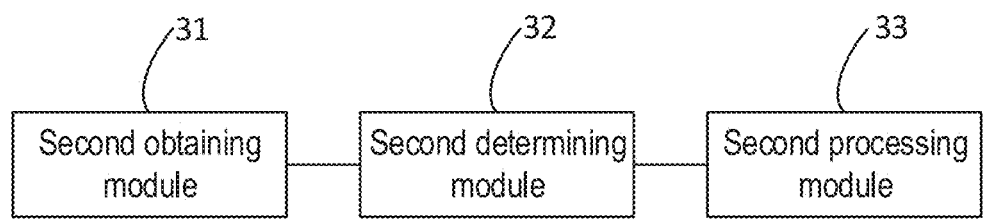
FIG. 19 is a block diagram illustrating a data processing apparatus according to some embodiments of the disclosure.

FIG. 19 is a block diagram illustrating a data processing apparatus according to some embodiments of the disclosure. In some embodiments, the data processing apparatus is configured to perform the afore-described data processing methods. In one embodiment, and as shown in FIG. 19, the apparatus includes a second obtaining module (31), a second determining module (32), and a second processing module (33).

The second obtaining module (31) is configured to obtain a data search request, the data search request being used for performing data searches on data of at least two different modalities.

The second determining module (32) is configured to determine at least one data search model corresponding to the data search request.

The second processing module (33) is configured to determine at least one search result corresponding to the data search request using the data search model.

In some embodiments, when the data search request includes search data of at least one modality, to determine at least one search result corresponding to the data search request using the data search model, the second processing module (33) is further configured to: obtain a feature extraction model corresponding to the search data; perform a feature extraction operation on the search data using the feature extraction model to obtain data feature information corresponding to the search data; and determine at least one search result corresponding to the data search request using the data search model and the data feature information.

In some embodiments, the feature extraction model includes at least one of the following: a single-sourced model, the single-sourced model being used for performing a feature extraction operation on data of the same data modality; a multi-sourced model, the multi-sourced model being used for performing a feature extraction operation on data of at least two different data modalities; and a fusion model, the fusion model being used for performing a feature extraction operation on data of at least three different data modalities.

In some embodiments, when a plurality of search results exist, the second processing module (33) is further configured to display the plurality of search results in a preset order.

In some embodiments, the second processing module (33) is further configured to perform data mining on the at least one search result to obtain an analysis result corresponding to the search result.

In some embodiments, performing data mining on the at least one retrieval result includes at least one of the following: statistical analysis and reasoning analysis.

According to various embodiments, the apparatus shown of FIG. 19 is configured to perform the methods of FIG. 13 to FIG. 16. Details illustrated with references to FIG. 13 to FIG. 16 are not repeated.

Figure 20:
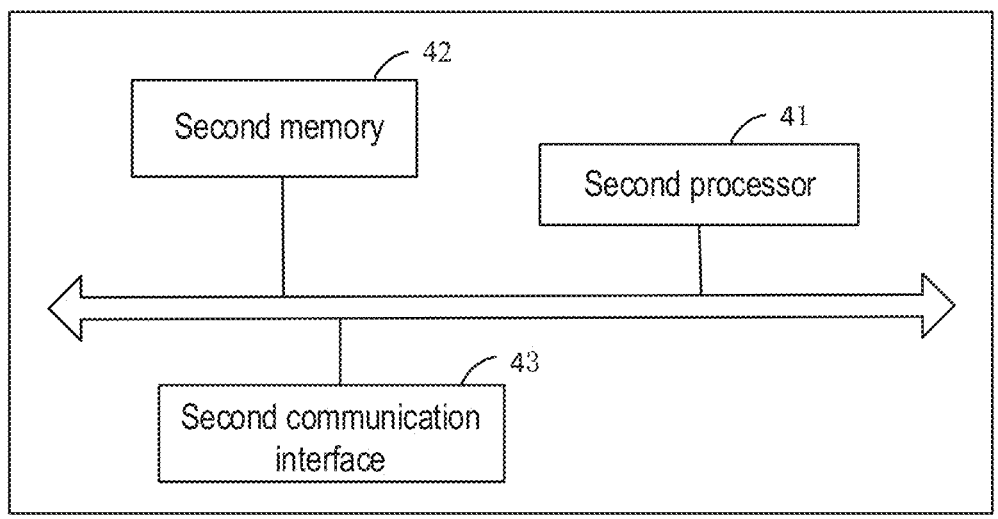
FIG. 20 is a block diagram illustrating an electronic device corresponding to the data processing apparatus of FIG. 19, according to some embodiments of the disclosure.

FIG. 20 is a block diagram illustrating an electronic device according to some embodiments of the disclosure. In some embodiments, the electronic device is configured to implement the apparatus of FIG. 19. In some embodiments, the electronic device is a mobile phone, a tablet computer, a server, or the like. In one embodiment, and as shown in FIG. 20, the electronic device includes a first processor (41) and a first memory (42). The first memory (42) is configured to store a program that, when executed, instructs the electronic device to perform the data processing method provided in the embodiments of FIG. 13 to FIG. 16. The first processor (41) is configured to execute the program stored in the first memory (42).

The program includes one or more of computer instructions, when executed by the second processor (41), implement the following steps.

Step 1: obtaining a data search request, the data search request being used for performing data searches on data of at least two different modalities.

Step 2: determining at least one data search model corresponding to the data search request.

Step 3: determining at least one search result corresponding to the data search request using the data search model.

In some embodiments, the electronic device further includes a second communication interface (43) for communicating with other devices or communication networks.

Further, embodiments of the disclosure provides a computer storage medium for storing computer software instructions executed by an electronic device, the computer storage medium including a program for performing the data processing methods of FIG. 13 to FIG. 16.

The apparatus embodiments described above are only schematic. The units described as separate components may or may not be physically separated, and the components displayed as units may or may not be physical units, that is, may be located at the same place, or may be distributed in a plurality of network units. The objective of the solution of this embodiment may be implemented by selecting some or all of the modules according to actual requirements. Those of ordinary skill in the art could understand and implement the disclosure without creative efforts.

Through the preceding description of the embodiments, those skilled in the art can clearly understand that the implementation manners can be implemented by software plus a necessary general hardware platform, and certainly can also be implemented by a combination of hardware and software. Based on such understanding, the above technical solution essentially or the portion contributing to the current system may be embodied in the form of a computer product. The disclosure may adopt the form of a computer program product implemented on one or a plurality of computer-usable storage media (including but not limited to a magnetic disk storage, a CD-ROM, an optical storage, etc.) containing computer-usable program code therein.

The disclosure is described with reference to flowcharts and/or block diagrams of a method, a device (system), and a computer program product according to the embodiments of the disclosure. It should be understood that each procedure and/or block in the flowcharts and/or block diagrams, and a combination of procedures and/or blocks in the flowcharts and/or block diagrams may be implemented with computer program instructions. These computer program instructions may be provided to a processor of a general-purpose computer, a special-purpose computer, an embedded processor, or any other programmable device to produce a machine, so that instructions executed by the processor of the computer or other programmable device generate means for implementing a specified function in one or a plurality of procedures in the flowcharts and/or one or a plurality of blocks in the block diagrams.

These computer program instructions may also be stored in a computer-readable memory that can direct a computer or any other programmable device to operate in a particular manner, such that the instructions stored in the computer-readable memory produce an article of manufacture including instruction means, the instruction means implementing a specified function in one or a plurality of procedures in the flowcharts and/or one or a plurality of blocks in the block diagrams.

These computer program instructions may also be loaded onto a computer or any other programmable device so that a series of operational steps are performed on the computer or other programmable device to produce computer-implemented processing, and thus the instructions executed on the computer or other programmable device provide the steps for implementing a specified function in one or a plurality of procedures in the flowcharts and/or one or a plurality of blocks in the block diagrams.

In a typical configuration, the computing device includes one or a plurality of processors (CPUs), input/output interfaces, network interfaces, and memories.

The memory may include a computer-readable medium in the form of a non-permanent memory, a random access memory (RAM) and/or non-volatile memory or the like, such as a read-only memory (ROM) or a flash memory (flash RAM). The memory is an example of the computer-readable medium.

The computer-readable medium includes permanent and non-permanent, movable and non-movable media that can achieve information storage by means of any methods or techniques. The information may be a computer-readable instruction, a data structure, a module of a program, or other data. Examples of a storage medium of a computer include, but are not limited to, a phase change memory (PRAM), a static random access memory (SRAM), a dynamic random access memory (DRAM), other types of random access memories (RAMs), a read-only memory (ROM), an electrically erasable programmable read-only memory (EEPROM), a flash memory or other memory technologies, a compact disk read-only memory (CD-ROM), a digital versatile disc (DVD) or other optical storages, a cassette tape, a magnetic tape/magnetic disk storage or other magnetic storage devices, or any other non-transmission medium, and can be used to store information accessible by a computing device. According to the definitions herein, the computer-readable medium does not include transitory computer-readable media (transitory media), such as a modulated data signal and a carrier wave.

It should be finally noted that the above embodiments are merely used for illustrating rather than limiting the technical solutions of the disclosure. Although the disclosure is described in detail with reference to the foregoing embodiments, those of ordinary skill in the art should understand that the technical solutions recorded in the foregoing embodiments may still be modified or equivalent replacement may be made on part or all of the technical features therein. These modifications or replacements will not make the essence of the corresponding technical solutions be departed from the spirit and scope of the technical solutions in the embodiments of the disclosure.

The invention claimed is:

1. A method comprising:
    obtaining data of at least two different modalities, the data comprising at least first data and second data, the first data and second stored in respective data sources, the at least two different modalities selected from a group consisting of image and text modalities;
    determining an overlapping keyword correlating the first data and the second data by analyzing textual descriptions associated with the first data and second data and identifying the overlapping keyword as appearing in a textual description of the first data and in a textual description of the second data;
    storing the first data and the second data in an associative manner based on the overlapping keyword, the associative manner generated using the overlapping keyword;
    annotating the first data to obtain a first annotation result after storing the first data and the second data;
    annotating the second data to obtain a second annotation result;
    performing a correlation annotation on the first data and the second data to obtain annotated correlation information; and
    training at least one machine learning (ML) model using the first data, the second data, and the overlapping keyword.

2. The method of claim 1, the storing the first data and the second data comprising:
    obtaining first clean data corresponding to the first data and second clean data corresponding to the second data; and
    storing the first clean data and the second clean data in the associative manner using the overlapping keyword.

3. The method of claim 2, further comprising:
    establishing a single-sourced model based on the first clean data and the first annotation result, or the second clean data and the second annotation result, the single-sourced model being used for performing a feature extraction operation on data of the same data modality; and
    storing the single-sourced model in a preset model library.

4. The method of claim 3, the feature extraction operation comprising extracting one or more of:
    basic features comprising one or more of data attribute information and data description information; and
    representative features comprising one or more of a feature graph and a feature vector.

5. The method of claim 3, further comprising:
    establishing a multi-sourced model based on the first clean data, the first annotation result, the second clean data, the second annotation result, a correlation annotation result, and the overlapping keyword, the multi-sourced model being used for performing an operation of extracting composite features among data of at least two different data modalities, and the composite features being used for characterizing a degree of correlation among the data of at least two different data modalities; and
    storing the multi-sourced model in the preset model library.

6. The method of claim 5, further comprising:
    establishing a fusion model based on the basic features, the representative features, and the composite features, the fusion model being used for performing a feature extraction operation on data of at least three different data modalities; and
    storing the fusion model in the preset model library.

7. The method of claim 6, further comprising:
    obtaining data and a data modality corresponding to the data for analysis;
    determining a feature extraction model corresponding to the data based on the data modality, the feature extraction model comprising at least one of the following: the single-sourced model, the multi-sourced model, and the fusion model; and
    performing a feature extraction operation on the data using the feature extraction model to obtain a feature extraction result corresponding to the data.

8. The method of claim 1, further comprising:
    obtaining a data de-sensitization request for the first data and the second data;
    identifying sensitive data corresponding to the data de-sensitization request in the first data and the second data; and
    performing data de-sensitization on the sensitive data.

9. A device comprising:
    a processor; and
    a storage medium for tangibly storing thereon program logic for execution by the processor, the stored program logic comprising:
        logic, executed by the processor, for obtaining data of at least two different modalities, the data comprising at least first data and second data, the first data and second stored in respective data sources, the at least two different modalities selected from a group consisting of image and text modalities,
        logic, executed by the processor, for determining an overlapping keyword correlating the first data and the second data by analyzing textual descriptions associated with the first data and second data and identifying the overlapping keyword as appearing in a textual description of the first data and in a textual description of the second data, logic, executed by the processor, for storing the first data and the second data in an associative manner based on the overlapping keyword, the associative manner generated using the overlapping keyword, logic, executed by the processor, for annotating the first data to obtain a first annotation result after storing the first data and the second data, logic, executed by the processor, for annotating the second data to obtain a second annotation result, logic, executed by the processor, for performing a correlation annotation on the first data and the second data to obtain annotated correlation information, and training at least one machine learning (ML) model using the first data, the second data, and the overlapping keyword.

10. The device of claim 9, the logic for storing the first data and the second data comprising:

logic, executed by the processor, for obtaining first clean data corresponding to the first data and second clean data corresponding to the second data, and logic, executed by the processor, for storing the first clean data and the second clean data in the associative manner using the overlapping keyword.

11. The device of claim 10, the stored program logic further comprising:

logic, executed by the processor, for establishing a single-sourced model based on the first clean data and the first annotation result, or the second clean data and the second annotation result, the single-sourced model being used for performing a feature extraction operation on data of the same data modality, and logic, executed by the processor, for storing the single-sourced model in a preset model library.

12. The device of claim 11, the stored program logic further comprising:

logic, executed by the processor, for establishing a multi-sourced model based on the first clean data, the first annotation result, the second clean data, the second annotation result, a correlation annotation result, and the overlapping keyword, the multi-sourced model being used for performing an operation of extracting composite features among data of at least two different data modalities, and the composite features being used for characterizing a degree of correlation among the data of at least two different data modalities, and logic, executed by the processor, for storing the multi-sourced model in the preset model library.

13. A non-transitory computer-readable storage medium for tangibly storing computer program instructions capable of being executed by a computer processor, the computer program instructions defining the steps of:

obtaining data of at least two different modalities, the data comprising at least first data and second data, the first data and second stored in respective data sources, the at least two different modalities selected from a group consisting of image and text modalities;

determining an overlapping keyword correlating the first data and the second data by analyzing textual descriptions associated with the first data and second data and identifying the overlapping keyword as appearing in a textual description of the first data and in a textual description of the second data;

storing the first data and the second data in an associative manner based on the overlapping keyword, the associative manner generated using the overlapping keyword;

annotating the first data to obtain a first annotation result after storing the first data and the second data;

annotating the second data to obtain a second annotation result;

performing a correlation annotation on the first data and the second data to obtain annotated correlation information; and training at least one machine learning (ML) model using the first data, the second data, and the overlapping keyword.

14. The computer-readable storage medium of claim 13, the storing the first data and the second data comprising:

obtaining first clean data corresponding to the first data and second clean data corresponding to the second data; and storing the first clean data and the second clean data in the associative manner using the overlapping keyword.

15. The computer-readable storage medium of claim 14, the computer program instructions further defining the steps of:

establishing a single-sourced model based on the first clean data and the first annotation result, or the second clean data and the second annotation result, the single-sourced model being used for performing a feature extraction operation on data of the same data modality; and storing the single-sourced model in a preset model library.

16. The computer-readable storage medium of claim 15, the computer program instructions further defining the steps of:

establishing a multi-sourced model based on the first clean data, the first annotation result, the second clean data, the second annotation result, a correlation annotation result, and the overlapping keyword, the multi-sourced model being used for performing an operation of extracting composite features among data of at least two different data modalities, and the composite features being used for characterizing a degree of correlation among the data of at least two different data modalities; and storing the multi-sourced model in the preset model library.

17. The computer-readable storage medium of claim 16, the computer program instructions further defining the steps of:

establishing a fusion model based on the basic features, the representative features, and the composite features, the fusion model being used for performing a feature extraction operation on data of at least three different data modalities; and storing the fusion model in the preset model library.

* * * * *